United States Patent
Ahn et al.

(10) Patent No.: US 8,702,966 B2
(45) Date of Patent: Apr. 22, 2014

(54) BIOSENSOR PROVIDED WITH CODE ELECTRODE, METHOD FOR MANUFACTURING THE SAME, AND METHOD FOR OBTAINING SENSOR INFORMATION FROM THE SAME

(75) Inventors: Yon Chan Ahn, Uiwang-si (KR); Mi Suk Park, Uiwang-si (KR); Min Seok Cha, Seoul (KR); Hye Sook Jung, Seoul (KR)

(73) Assignee: All Medicus Co., Ltd., Anyang-si (KR)

( * ) Notice: Subject to any disclaimer, the term of this patent is extended or adjusted under 35 U.S.C. 154(b) by 38 days.

(21) Appl. No.: 13/121,539

(22) PCT Filed: Jun. 30, 2009

(86) PCT No.: PCT/KR2009/003536
§ 371 (c)(1),
(2), (4) Date: Mar. 29, 2011

(87) PCT Pub. No.: WO2010/095787
PCT Pub. Date: Aug. 26, 2010

(65) Prior Publication Data
US 2012/0142117 A1    Jun. 7, 2012

(30) Foreign Application Priority Data
Feb. 19, 2009    (KR) .................. 10-2009-0014057

(51) Int. Cl.
*G01N 27/327*    (2006.01)
*C12Q 1/54*    (2006.01)

(52) U.S. Cl.
USPC .................. 205/792; 205/777.5; 204/403.01; 204/403.11; 422/68.1; 422/82.01; 435/287.1; 29/847; 427/555

(58) Field of Classification Search
USPC ............... 204/403.01–403.15; 600/345–348; 205/775, 777.5, 778, 792; 435/287.1; 422/68.1, 82.01; 29/847; 427/555
See application file for complete search history.

(56) References Cited

U.S. PATENT DOCUMENTS

| | | | |
|---|---|---|---|
| 2003/0042150 A1* | 3/2003 | Ryu et al. ...................... | 205/778 |
| 2004/0060818 A1* | 4/2004 | Feldman et al. ......... | 204/403.01 |
| 2007/0110615 A1 | 5/2007 | Neel et al. | |
| 2007/0278097 A1* | 12/2007 | Bhullar et al. ........... | 204/403.01 |
| 2008/0020452 A1 | 1/2008 | Popovich et al. | |
| 2008/0021295 A1* | 1/2008 | Wang et al. .................. | 600/347 |
| 2010/0243441 A1* | 9/2010 | Groll ........................ | 204/403.01 |

FOREIGN PATENT DOCUMENTS

JP    2009-8574 A    1/2009
WO    WO 2008/040997    *    4/2008

OTHER PUBLICATIONS

International Search Report issued in PCT/KR2009/003536, mailed Oct. 27, 2009.

* cited by examiner

*Primary Examiner* — J. Christopher Ball
*Assistant Examiner* — Jennifer Dieterle
(74) *Attorney, Agent, or Firm* — Greer Burns & Crain Ltd.

(57) ABSTRACT

The present invention provides a biosensor having a code electrode, a method for manufacturing the same, and a method for obtaining sensor information on the same, in which a code electrode for providing sensor information such as correction information, the type of biosensor, etc. is provided in each biosensor such that a measuring device can obtain necessary information on each biosensor from the code electrode, thus solving a variety of conventional problems.

20 Claims, 15 Drawing Sheets

BIOSENSOR PROVIDED WITH CODE ELECTRODE, METHOD FOR MANUFACTURING THE SAME, AND METHOD FOR OBTAINING SENSOR INFORMATION FROM THE SAME

This application is a U.S. National Phase under 35 U.S.C. §371 of International Application No. PCT/KR2009/003536, filed Jun. 30, 2009.

TECHNICAL FIELD

The present invention relates to a biosensor, a method for manufacturing the same, and a method for obtaining sensor information on the same and, more particularly, to a biosensor having a code electrode, a method for manufacturing the same, and a method for obtaining sensor information on the same, in which a code electrode for providing sensor information such as correction information, the type of biosensor, etc. is provided in each biosensor such that a measuring device can obtain necessary information on each biosensor from the code electrode, thus solving a variety of conventional problems.

BACKGROUND ART

A biosensor is a device that converts information on an analyte into a detectable signal such as a color, fluorescent, or electrical signal using a biological component or imitating the biological component.

Especially, since a biosensor that utilizes a biological enzyme has excellent sensitivity and reaction specificity, it is expected that it will be useful in a wide range of applications such as medical/pharmaceutical field, process measurement in bio-industry, environmental measurement, stability evaluation of chemical materials, etc.

Measurement of chemical components in vitro is medically important, and thus the biosensors are widely used in the analysis of biological samples such as blood in the medical diagnosis field.

Among them, a biosensor using an enzyme analysis method in which a specific reaction between an enzyme and a substrate or between an enzyme and an inhibitor is used has advantages of simple application, excellent detection sensitivity, and fast response, and thus it is most widely used in hospitals and clinical chemistry analysis.

The enzyme analysis method for the measurement of chemical components in vitro may be classified into a chromatogenic method for measuring optical transmittance by a spectroscopic method before and after an enzyme reaction, and an electrode method for measuring an electrochemical signal.

Compared to the electrode method, the chromatogenic method has difficulties in analyzing critical biomaterials because the measurement time is long, a large amount of sample is required, and measurement errors occur due to turbidity in biological samples.

Therefore, the electrode method, in which an electrode system including a plurality of electrodes is formed on a plastic film (insulating substrate) and a reagent is fixed on the electrodes such that a specific substance in a sample can be quantitatively measured by applying a predetermined electric potential to the sample, has been widely applied to the biosensor using the enzyme analysis method.

In the case where the electrode method is employed, a measuring device for obtaining information on biological samples from the biosensor is required, and the measuring device includes a socket electrically connected to thin film electrodes of the biosensor.

Accordingly, when the thin film electrodes of the biosensor are inserted into the measuring device through an inlet port, the thin film electrodes are connected to terminals formed in the socket of the measuring device such that the measuring device in an ON state receives information on the biological material as an analyte from the biosensor.

One of the most widely used biosensors employing the electrode method is a blood glucose meter, with which everyone can measure the concentration of glucose (sugar) in blood by easily taking a drop of blood.

In the case of insulin-dependent diabetics who should measure blood glucose two to three times a day, they take a drop of blood by pricking a finger with a lancet to measure blood glucose. At this time, the blood glucose meter is used to measure blood glucose level from an electrical signal generated by an electrochemical reaction between a reactant in the biosensor and a sample (e.g., blood) taken from a diabetic.

That is, an enzyme reaction layer including a hydrophilic polymer, an oxidoreductase and an electron acceptor is formed on an electrode system of the biosensor such that, when a user injects a sample (blood) containing a substrate (glucose) through a sample inlet port of the biosensor to come in contact with the enzyme reaction layer, the enzyme reaction layer dissolves the sample, the substrate in the sample reacts with an enzyme and is oxidized, and thus the electron acceptor is reduced. At this time, an oxidation current obtained when the reduced electron acceptor is electrochemically oxidized is measured by the measuring device, thereby obtaining the concentration of the substrate contained in the sample.

FIGS. 1 and 2 are diagrams showing a basic configuration of an electrochemical biosensor, in which FIG. 1 is an exploded perspective view and FIG. 2 is an assembly perspective view.

As shown in FIGS. 1 and 2, a biosensor (also referred to as a test strip) 10 includes a working electrode 12 and a reference electrode 13, which are stacked on an upper surface (i.e., inner surface) of a lower insulating substrate 11 in the longitudinal direction, and an enzyme reaction layer, i.e., a reagent reaction layer 14 is fixed on the working electrode 12 and the reference electrode 13 in the width direction. The electrodes 12 and 13 are formed by a thin film formation process such as etching, screen printing, or sputtering.

Moreover, spacers 15 and 16 are stacked on the lower insulating substrate 11 on which the electrodes 12 and 13 are formed such that a sample (e.g., blood) is appropriately introduced into the entire enzyme reaction layer 14. Then, an upper insulating substrate 17 is stacked on the spacers 15 and 16 such that the upper and lower insulating substrates 17 and 11, spaced from each other by the spacers 15 and 16, form a sample path 18 having a capillary structure on the enzyme reaction layer 14.

In this case, the working electrode 12 and the reference electrode 13 are insulated from each other by the spacers 15 and 16, and an inlet of the sample path 18, formed by the upper and lower insulating substrates 17 and 11 through the spacers 15 and 16, corresponds to a sample inlet port 18a through which the sample is injected.

Moreover, each end of the working electrode 12 and the reference electrode 13 is exposed at a connection terminal of the biosensor 10 such that they can be connected to terminals formed in a socket of a measuring device (not shown) when the biosensor 10 is inserted into the measuring device.

Meanwhile, the biosensor (test strip) has an unavoidable error in itself due to various factors. Thus, during manufacturing process of the biosensor, it is determined whether the measurement is accurate or how large the error range is in each biosensor.

Moreover, since it is necessary to correct the error that each biosensor has in order to obtain more accurate measurement, the measuring device receives correction information from the biosensor and corrects the measured value of the biosensor using the correction information, thus displaying a final result value.

For this purpose, a process of inputting the correction information to the measuring device is required due to the error that each biosensor has such that the measuring device can correct the measured value of the biosensor based on the correction information input to the measuring device and display an accurate result value.

For example, the correction information is input to the measuring device in advance such that the measuring device can display a result value obtained by reflecting a correction value (based on the correction information) on the measured value of the corresponding biosensor during measurement. That is, in the case where a blood glucose reference value is 100, if a measured value of a first biosensor is 100, code A is assigned. If a measured value of a second biosensor is 90, code B is assigned to add a correction value of 10, thus making 100. If a measured value of a third biosensor is 110, code C is assigned to subtract 10 from 110, thus making 100. As such, when one of the biosensors is used, a code (indicating the correction information) is input to the measuring device in advance such that the measuring device can display a result value obtained by reflecting the correction value based on the input correction information on the measured value of the corresponding biosensor during the next measurement.

As a conventional method of inputting the correction information to the measuring device, a method of using bar codes is typically used.

That is, after manufacturing biosensors, the manufacturing company obtains correction information by determining error ranges, classifies the biosensors into those having the same correction information (e.g., classified into A, B, and C codes), and contains the biosensors having the same correction information in the same container. Then, the manufacturing company attaches a bar code indicating the corresponding correction formation to the container in which the biosensors having the same correction information are contained and provides the container to a user as a product. Accordingly, the user who has purchased the product reads the bar code attached to the container using a bar code scanner connected to a measuring device and inputs the correction information of the purchased biosensor to the measuring device that the user has.

As a result, the measuring device corrects the measured value of the biosensor based on the correction information input by the bar code scanner during each measurement and displays an accurate result value.

In the above method of using bar codes, a bar code containing a variety of sensor information such as manufacturing date, expiration date, and the type of biosensors contained in the same container as well as the correction information can be printed. Of course, in this case, the biosensors contained in the same container should have the same manufacturing date and expiration date as well as the correction information.

However, the conventional method of using bar codes has the following problems.

In order to input the sensor information including the correction information, it is necessary to read the bar code containing the sensor information, i.e. the bar code attached to the container, and it is thus necessary to connect a scanner to the measuring device, which results in an increase in the price of the measuring device.

Moreover, a biosensor having different sensor information including correction information and the like may be contained in the same container due to carelessness of the manufacturing company or the user. Especially, in the case where the biosensor having different correction information is used by mistake, an accurate correction value of the corresponding biosensor is not reflected (instead, a correction value of the corresponding bar code is reflected), and thereby a measurement error may occur.

DISCLOSURE OF THE INVENTION

Problems to be Solved by the Invention

Accordingly, the present invention has been made to solve the above-describe problems, and an object of the present invention is to provide a biosensor having a code electrode, a method for manufacturing the same, and a method for obtaining sensor information on the same, in which a code electrode for providing sensor information such as correction information, the type of biosensor, etc. is provided in each biosensor such that a measuring device can obtain necessary information on each biosensor from the code electrode, thus solving a variety of conventional problems.

Means for Solving the Problems

To accomplish the above objects of the present invention, there is provided a biosensor, in which a working electrode and a reference electrode are formed on an inner surface of a lower insulating substrate, a reagent reaction layer is fixed on the inner surface of the lower insulating substrate along a sample path to be in contact with the working electrode and the reference electrode, and an upper insulating substrate is assembled with the lower insulating substrate with spacers interposed therebetween to form the sample path, wherein a code electrode formed to be in contact with the reagent reaction layer, outputting an electrical signal according to a reaction between a sample and a reagent, and providing the signal to a measuring device as sensor information is additionally provided in the inside of the biosensor, wherein the code electrode comprises a code pattern portion, formed by patterning the code electrode at a position which is in contact with the reagent reaction layer, so as to output the electrical signal according to the sensor information, and wherein the code pattern portion is patterned by removing a predetermined area of the code electrode such that the contact area with the reagent reaction layer, in which reaction current flows, differs according to a code assigned to the corresponding biosensor based on the sensor information.

Moreover, the present invention provides a method for manufacturing a biosensor having a code electrode, the method comprising: forming a working electrode, a reference electrode, and a code electrode on an inner surface of a lower insulating substrate; fixing a reagent reaction layer on the inner surface of the lower insulating substrate along a sample path to be in contact with the working electrode, the reference electrode, and the code electrode; forming a code pattern portion by pattering a specific region of the code electrode, which is in contact with the reagent reaction layer, according to a code assigned to a corresponding biosensor based on sensor information; and assembling an upper insulating substrate with the lower insulating substrate with a spacer interposed therebetween to form the sample path, wherein the code pattern portion is patterned by removing a predetermined area of the code electrode such that the contact area with the reagent reaction layer, in which reaction current flows, differs according to the assigned code.

Furthermore, the present invention provides a method for manufacturing a biosensor having a code electrode, the method comprising: forming a working electrode and a reference electrode on an inner surface of a lower insulating substrate; fixing a reagent reaction layer on the inner surface of the lower insulating substrate along a sample path to be in contact with the working electrode and the reference electrode; forming a code electrode, which is in contact with the reagent reaction layer, on an inner surface of an upper insulating substrate; forming a code pattern portion by patterning a specific region of the code electrode, which is in contact with the reagent reaction layer, according to a code assigned to a corresponding biosensor based on sensor information; and assembling the upper insulating substrate with the lower insulating substrate with a spacer interposed therebetween to form the sample path, wherein the code pattern portion is patterned by removing a predetermined area of the code electrode such that the contact area with the reagent reaction layer, in which reaction current flows, differs according to the assigned code.

In addition, the present invention provides a method for manufacturing a biosensor having a code electrode, the method comprising: forming a working electrode and a reference electrode on an inner surface of a lower insulating substrate; forming a second code electrode portion on the inner surface of the lower insulating substrate such that one end thereof is connected to an intermediate conductive portion of a spacer and the other end thereof is connected to a socket terminal of a measuring device; fixing a reagent reaction layer on the inner surface of the lower insulating substrate along a sample path to be in contact with the working electrode and the reference electrode; forming a first code electrode portion, which is in contact with the reagent reaction layer, on an inner surface of an upper insulating substrate; forming a code pattern portion by patterning a specific region of the first code electrode portion, which is in contact with the reagent reaction layer, according to a code assigned to a corresponding biosensor based on sensor information; fixing the intermediate conductive portion on the spacer; and assembling the upper insulating substrate with the lower insulating substrate with the spacer interposed therebetween to form the sample path such that the intermediate conductive portion of the spacer connects the first code electrode portion and the second code electrode portion, wherein the code pattern portion is patterned by removing a predetermined area of the first code electrode portion such that the contact area with the reagent reaction layer, in which reaction current flows, differs according to the assigned code.

Additionally, the present invention provides a method for obtaining sensor information on a biosensor having a code electrode, the method comprising: providing a biosensor including a working electrode, a reference electrode, a code electrode, and a reagent reaction layer fixed on the electrodes along a sample path to be in contact with the electrodes; applying working voltage to the working electrode and injecting a sample into the sample path after the biosensor is inserted into a measuring device; and obtaining sensor information on the corresponding biosensor based on electrical signals output from the working electrode and the code electrode.

Effect of the Invention

Thus, according to the present invention, a code electrode for providing sensor information such as correction information, the type of biosensor, etc. is provided in each biosensor such that a measuring device can obtain necessary information on each biosensor from the code electrode, thus solving a variety of conventional problems.

Especially, since the biosensor includes the code electrode in itself and thus can directly provide a variety of information to the measuring device during the use of the biosensor, it is possible to solve the problems associated with the use of a bar code or scanner. Moreover, it is possible to improve the product value of biosensors. Further, since each biosensor can provide accurate sensor information to the measuring device, it is possible to improve the accuracy of measurement.

To perform the measurement, the measuring device may be equipped with only simple socket terminals capable of recognizing signals of the code electrode, and it is thus possible to obtain the information on each sensor provided by the code electrode through the socket terminals.

Moreover, the biosensor having the code electrode can be used in various applications. For example, it is possible to prevent a code recognition error and determine the characteristics of the sample by providing a sensing electrode for detecting the sample, for example, in the biosensor.

BRIEF DESCRIPTION OF THE DRAWINGS

FIGS. 1 and 2 are diagrams showing a basic configuration of a conventional biosensor, in which FIG. 1 is an exploded perspective view and FIG. 2 is an assembled perspective view.

BEST MODE FOR CARRYING OUT THE INVENTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention provides a biosensor having a code electrode for providing sensor information, a method for manufacturing the biosensor, and a method for obtaining sensor information on the biosensor. In the following specification, the sensor information may include a variety of information, such as correction information, the type of biosensor, etc., required by a measuring device, and an electrode which is provided in each biosensor to provide such sensor information will be referred to as the code electrode.

Figure 1:
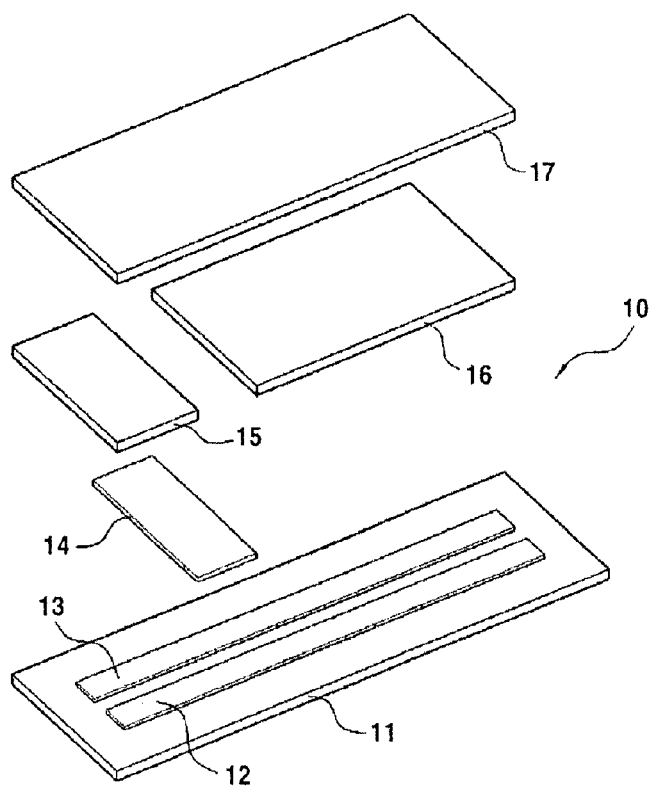
Figure 2:
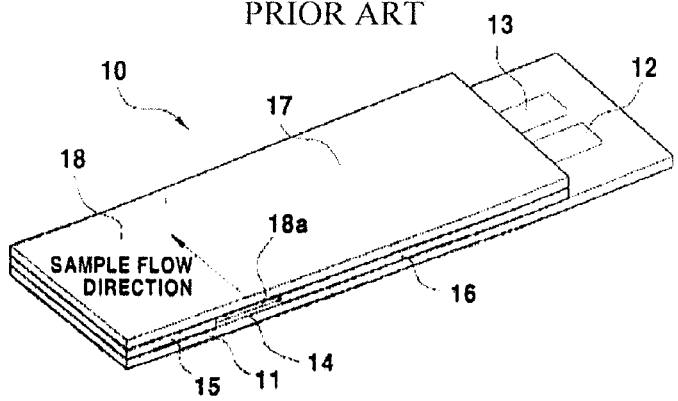
Figure 3:
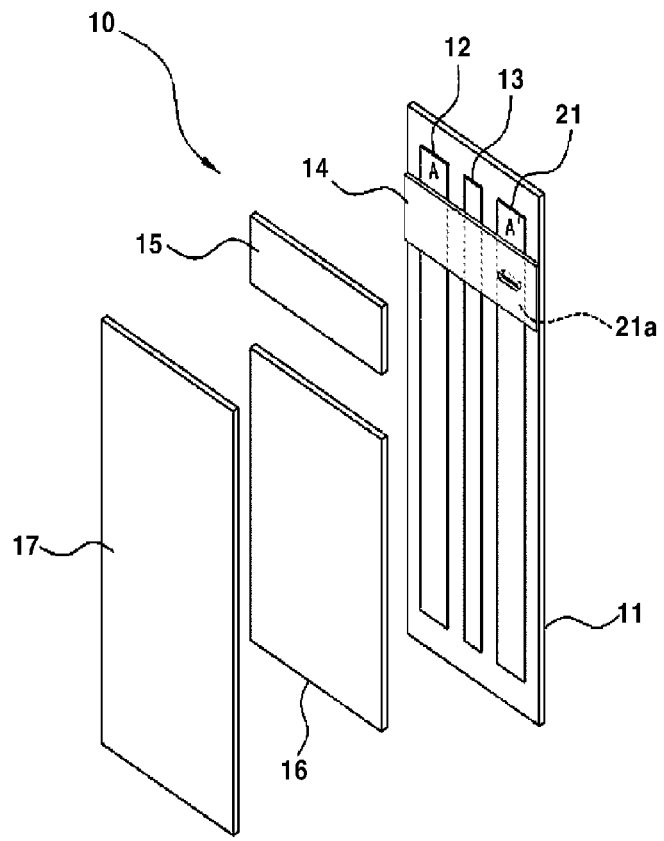
FIGS. 3, 5 and 6 are exploded perspective views of a biosensor in accordance with a preferred embodiment of the present invention.
Figure 4:
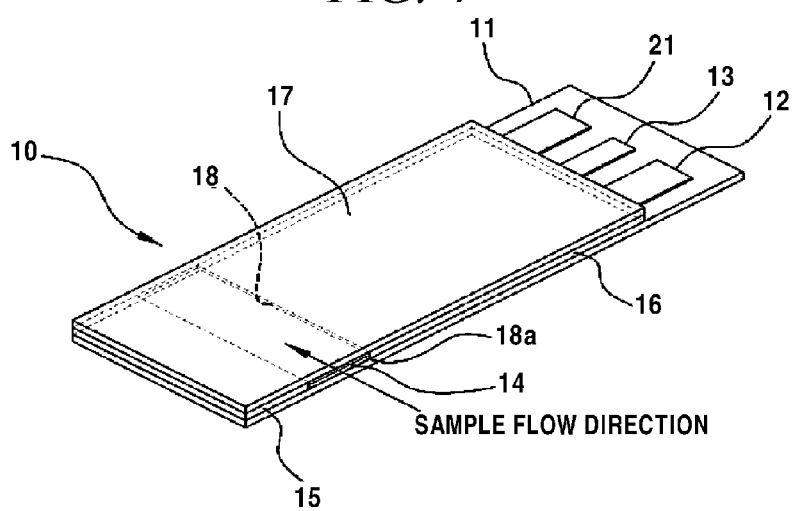
FIG. 4 is an assembled perspective view of the biosensor shown in FIG. 3.

FIG. 3 is an exploded perspective view of a biosensor 10 in accordance with a preferred embodiment of the present invention, and FIG. 4 is an assembled perspective view of the biosensor 10 shown in FIG. 3.

As shown in FIGS. 3 and 4, a working electrode 12 and a reference electrode 13 are stacked on an upper surface (i.e. inner surface) of a lower insulating substrate 11 in the longitudinal direction so as to output an electrical signal generated by a reaction between a sample and a reagent when working voltage is applied thereto, i.e., an electrical signal according to the concentration of a specific component in the sample. Further, a reagent reaction layer 14 is fixed on the working electrode 12 and the reference electrode 13 (along a sample path) to intersect the electrodes.

Spacers 15 and 16 are stacked on the lower insulating substrate 11 and an upper insulating substrate 17 is stacked on the spacers 15 and 16 such that the lower and upper substrates 11 and 17, spaced from each other by the spacers 15 and 16, form a sample path 18 having a capillary structure on the reagent reaction layer 14.

Moreover, a code electrode 21 for providing sensor information is formed in the biosensor 10 to be in contact with the reagent reaction layer 14 in addition to the working electrode 12 and the reference electrode 13.

The code electrode 21 is formed of the same material as the working electrode 12 and the reference electrode 13 on the same surface of the lower insulating substrate 11. Also, the code electrode 21 is formed to pass through the sample path 18, in which the reagent reaction layer 14 is provided, in the same manner as the working electrode 12 and the reference electrode 13.

The code electrode 21 is also formed on the lower insulating substrate 11 in the longitudinal direction of the biosensor 10 and exposed at a connection terminal of the biosensor 10. And, the code electrode 21 partially exposed at the connection terminal of the biosensor 21 is connected to a terminal provided in a socket of a measuring device (not shown) when the biosensor 10 is inserted into an insertion hole of the measuring device, like the working electrode 12 and the reference electrode 13.

The code electrode 21 may be formed by a thin film formation process such as etching, screen printing, or sputtering, like the working electrode 12 and the reference electrode 13.

Meanwhile, the code electrode 21 has a patterned structure in which a specific region which is in contact with the reagent reaction layer 14 is removed. If the sample is the same one, an electrical signal output from the code electrode 21 varies according to the contact area (with the reagent reaction layer) of the code electrode 21 remaining after the specific region is removed.

That is, when the working voltage is applied to the working electrode 12 and the sample is injected into a sample inlet port 18a of the biosensor 10 after the biosensor 10 is inserted into the measuring device such that the respective electrodes are connected to the socket terminals of the measuring device, a current value that the measuring device reads from the code electrode 21 (i.e., current generated by a reaction between the sample and the reagent) varies according to the contact area between the reagent reaction layer 14 and the area of the code electrode 21 (i.e., the area of the code electrode corresponding to the reagent reaction layer in which a reaction current flows).

If the area of the code electrode 21 in the reagent reaction layer 14 in which the reaction current flows is the same in each biosensor 10, the same electrical signal may be output from the code electrode 21. However, if the area of the code electrode 21 that reacts with the reagent reaction layer 14 is different in each biosensor 10, there is a difference in the electrical signal output from the code electrode 21 of each biosensor 10.

Accordingly, when the area of each code electrode 21 (i.e., the area in which the reaction current flows) which is in contact with the reagent reaction layer 14 is different in each biosensor 10 after a plurality of biosensors 10 are classified according to the sensor information, the measuring device can identify the difference in the electrical signal output from the code electrode 21 during the next measurement and distinguish the biosensors 10 according to the sensor information.

As such, the present invention aims at providing the plurality of biosensors 10 in which the area of each code electrode 21 which is in contact with the reagent reaction layer 14 is different in each biosensor 10 according to the classification of the sensor information such that the measuring device can distinguish the biosensors 10 based on the sensor information according to the contact area information between the reagent reaction layer 14 and the code electrode 21.

For this purpose, the biosensors 10 are classified into A, B, and C codes, for example, according to the sensor information such as correction information, the type of biosensor, etc., which the measuring device can distinguish, after the code electrodes 21 are formed during manufacturing of the biosensors 10. Then, the area of the code electrode 21 in each biosensor 10 which is in contact with the reagent reaction layer 14 is subjected to a patterning process, and the resulting area of the code electrode 21 differs in each biosensor 10 according to the sensor information.

In more detail, after the working electrode 12, the reference electrode 13, and the code electrode 21 are formed on the lower insulating substrate 11, the reagent reaction layer 14 is fixed in the width direction of the biosensor 10 to be in contact with the respective electrodes. Then, a code is assigned to each biosensor classified according to the sensor information such as correction information, the type of biosensor, etc., and the patterning process of removing a specific region of the code electrode 21 which is in contact with the reagent reaction layer 14 is carried out according to the assigned code.

In this case, a predetermined area is removed from the code electrode based on the assigned code. That is, the area determined for each code is removed such that the area of the code electrode remaining after the patterning process differs according to the assigned code.

In the process of manufacturing the biosensor 10 of the present invention, the specific region of the code electrode 21 may be removed by a laser ablation process.

Figure 5:
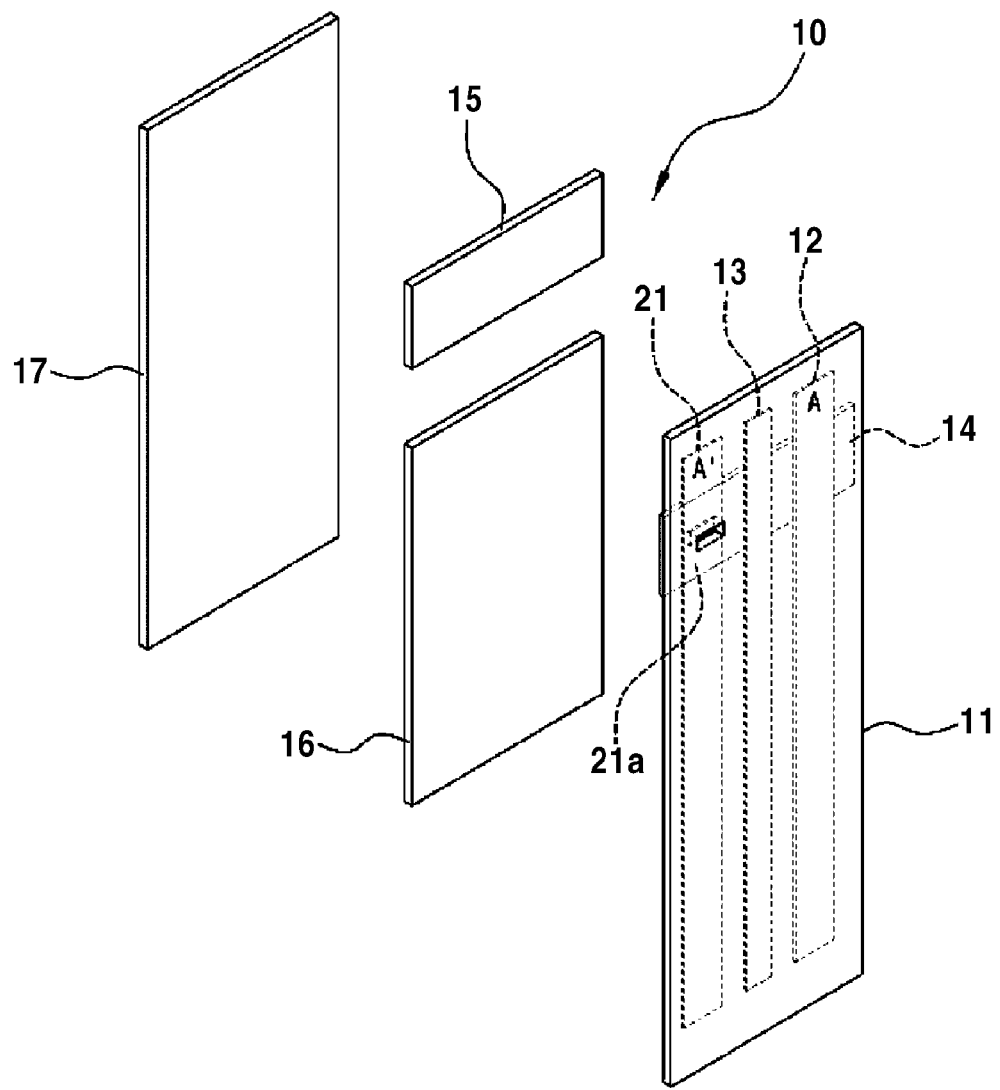

As shown in FIG. 3, the code electrode 21 may be patterned on a front surface (i.e., upper surface or inner surface) of the lower insulating substrate 11 using the laser ablation process. Alternatively, as shown in FIG. 5, the code electrode 21 may be patterned on a rear surface (i.e., lower surface or outer surface) of the lower insulating substrate 11.

In more detail, as shown in FIG. 3, after the working electrode 12, the reference electrode 13, and the code electrode 21 are formed in the longitudinal direction of the lower insulating substrate 11, the reagent reaction layer 14 is fixed on the electrodes in the width direction, and then a laser beam is irradiated from the front surface of the lower insulating substrate 11 so as to remove the specific region of the code electrode 21 together with the reagent reaction layer 14.

In this case, the reagent reaction layer 14 and the code electrode 21 are removed at a predetermined position in a predetermined area according to the assigned code of the corresponding biosensor 10, and the corresponding area of the lower insulating substrate 11 is left as it is. That is, only the area corresponding to the reagent reaction layer 14 and the code electrode 21 is removed.

In the process of patterning the code electrode 21, it is possible to employ a known laser apparatus capable of controlling the area of the surface of an object, to which a laser beam emitted from a light source is irradiated, and the area and depth of the object removed by the laser beam.

As shown in FIG. 5, the laser beam is irradiated from the rear surface of the lower insulating substrate 11 to remove the specific region of the code electrode 21 together with the lower insulating substrate 11. In this case, after the working electrode 12, the reference electrode 13, and the code electrode 21 are formed on the same lower insulating substrate 11, the specific region of the code electrode 21 is removed from the rear surface of the lower insulating substrate 11 together with the lower insulating substrate 11 using the laser beam.

At this time, the laser beam is irradiated from the rear surface of the lower insulating substrate 11 to remove the lower insulating substrate 11 and the code electrode 21 at a predetermined position in a predetermined area according to the assigned code of the corresponding biosensor 10. Only the corresponding area of the lower insulating substrate 11 and the code electrode 21 is removed, and the reagent reaction layer 14 is not removed. That is, only the area corresponding to the lower insulating substrate 11 and the code electrode 21 is removed such that the reagent reaction layer 14 may not be damaged.

Figure 6:
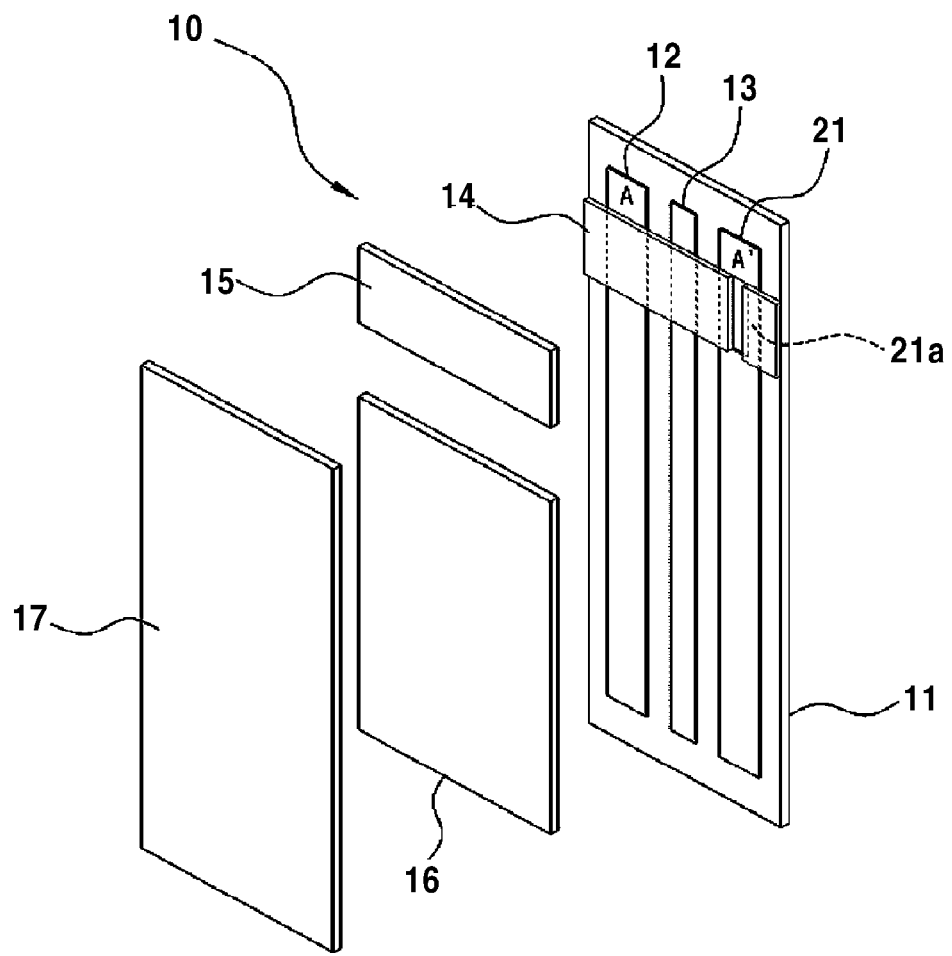

As such, in the process of forming the pattern for code recognition on the code electrode 21, the shape of the pattern of the code electrode 21 and the shape of the code electrode area removed by the laser beam are not limited. As shown in FIG. 3, a predetermined area in the width direction of the code electrode 21 may be removed using the laser beam. Alternatively, as shown in FIG. 6, a predetermined area in the longitudinal direction of the code electrode 21 may be removed using the laser beam. Otherwise, in order to remove a predetermined area, the code electrode 21 may be removed in both the length and width directions. Further, in order to remove a predetermined area, the code electrode 21 may be removed in one or two rows, or in a predetermined number of rows, if necessary.

In the case where a specific area of the code electrode 21 is removed in the width direction such that the code electrode 21 is cut into two parts, that is, in the case where the code electrode 21 which is in contact with the reagent reaction layer 14 is cut into two parts by the laser ablation, the two parts are electrically insulated from each other. Thus, a reaction current generated in the part (in the reagent reaction layer where the reaction current flows, which will be referred to as "Part-S") connected to the terminal of the measuring device is output. At this time, an electrical signal (current) according to an area of Part-S is output from the code electrode 21. Therefore, in this case, the area of Part-S is controlled to assign a code to the corresponding biosensor.

In the following specification, the part of the code electrode 21 in the reagent reaction layer 14 will be called "a code pattern portion" 21a for a clear understanding of the present invention. The code pattern portion 21a of the code electrode 21 in the biosensor 10 of the present invention has a patterned structure in which a specific region in a predetermined area is removed, which is directed to a (code providing) region that provides sensor information (code information) corresponding to the contact area with the reagent reaction layer 14 to the measuring device.

Accordingly, the measuring device can distinguish the biosensor by the electrical signal output from the code electrode 21 and recognize the code of the biosensor corresponding to the contact area between the code pattern portion 21a and the reagent reaction layer 14. That is, the measuring device can obtain the sensor information provided by the code pattern portion 21a of the biosensor. As such, in the biosensor of the present invention, when the predetermined area of the code electrode 21 in the reagent reaction layer 14 is removed to form the code pattern portion 21a, the code electrode 21 can provide the sensor information (corresponding to the area in which the reaction current flows) that the code pattern portion 21a has to the measuring device.

Meanwhile, in the biosensor 10 of the present invention, a process in which the measuring device obtains the sensor information from the code electrode 21, that is, a method for recognizing a code pattern of the code electrode 21 will be described below.

As mentioned above, the measuring device can recognize the code pattern of the code pattern portion 21a based on the electrical signal output from the code electrode 21. In the preferred embodiment, the measuring device can recognize the code pattern from an intensity ratio of the electrical signals output from the working electrode 12 and the code electrode 21 during the use (measurement) of the biosensor 10. The reason is that signals having the same intensity are output from the electrodes having the same area which are in contact with the reagent reaction layer 14. Especially, the method for recognizing the code pattern according to the present invention uses the signal change according to the change in the area ratio, in which the code pattern is identified using the ratio of the measured currents of the working electrode 12 and the code electrode 21.

In more detail, when the working voltage is applied to the working electrode 12 and the sample is injected into the sample inlet port 18a of the biosensor 10 after the biosensor 10 is inserted into the measuring device such that the respective electrodes are connected to the socket terminals of the measuring device, currents generated by the reaction between the sample and the reagent are output from the electrodes connected to the reagent reaction layer 14, especially from the working electrode 12 and the code electrode 21, as the electrical signals, and the measuring device can measure the currents.

At this time, the current output from the working electrode 12 and measured by the measuring device corresponds to the concentration of a specific component in the sample. For example, in the case of a blood glucose biosensor, the measured current is a signal corresponding to the concentration of glucose in the blood sample. Accordingly, the measuring device calculates blood glucose based on the current output from the working electrode 12 and displays the blood glucose to a user.

Moreover, when a current according to the contact area between the code pattern portion 21a and the reagent reaction layer 14 is output from the code electrode 21, the measuring device simultaneously measures the currents output from the working electrode 12 and the code electrode 21 to calculate a ratio of the measured currents from the two electrodes 12 and 21, and recognizes a corresponding code pattern from the ratio of the measured current.

Although the currents output from the working electrode 12 and the code electrode 21 are typically generated by the reaction between the sample and the reagent, the ratio of the two currents output from the working electrode 12 and the code electrode 21 corresponds to the ratio of the contact areas between the respective electrodes and the reagent reaction layer 14. That is, the ratio of the current measured at the working electrode 12 and the current measured at the code electrode 21 corresponds to the ratio of the area where the working electrode 12 is in contact with the reagent reaction layer 14 and the area where the code electrode 21 is in contact with the reagent reaction layer 14 (the current ratio between the two electrodes is equal to the area ratio).

As such, the measuring device recognizes the code of the biosensor by calculating the ratio of the currents measured at the two electrodes. Thus, it is necessary to fabricate the working electrode and the code electrode (especially, the code pattern portion of the code electrode) such that the area ratio between the working electrode 12 and the code electrode 21 in the reagent reaction layer 14 has a value corresponding to a code assigned to the biosensor during manufacturing of the biosensor 10. Moreover, it is necessary that predetermined code information (sensor information) according to the current ratio should be stored in advance in the measuring device such that the measuring device can recognize the code based on the current ratio when the current ratio according to the area ratio is calculated.

An example of the current ratios of the two electrodes (i.e., the area ratios of the two electrodes that are in contact with the reagent reaction layer) according to the codes in the biosensors of the present invention is as follows.

EXAMPLE

Code A if the current ratio of the working electrode and the code electrode is 1:1;

Code B if the current ratio of the working electrode and the code electrode is 1:1.08; and Code C if the current ratio of the working electrode and the code electrode is 1:1.05;

Although the above example shows that the ratios of the measured currents (i.e., the area ratios of the two electrodes) are classified into three codes, the number of codes may be variously changed, and the current ratios according to the respective codes may be variously changed as far as they can be distinguished by the measuring device.

Moreover, in the biosensor 10 of the present invention, the code electrode 21 may be formed in the same shape as the working electrode 12. In the above example, if the current ratio for a specific code is set to 1:1, it is possible to fabricate the working electrode and the code electrode in the same shape without removing a specific region from the code electrode and without forming a pattern to set a code of the corresponding biosensor. Since the working electrode and the code electrode have the same shape and contact area in the reagent reaction layer, the current ratio may be 1:1.

Referring to the embodiment of FIGS. 3, 5 and 6, it can be seen that the code electrode 21 having the same shape and size as the working electrode 12 is formed in parallel with the reference electrode 13 on the lower insulating substrate 11.

As such, in the present invention, the code electrode 21 is additionally formed in the biosensor 10 such that the measuring device can recognize the code of the corresponding biosensor using the intensity ratio of the signals output from the working electrode 12 and the code electrode 21 during the use of the biosensor 10. Here, the intensity ratio of the signals corresponds to the ratio of the currents measured at the working electrode 12 and the code electrode 21, and the ratio of the currents corresponds to the area ratio of the two electrodes that are in contact with the reagent reaction layer 14.

Moreover, in the present invention, the code electrode 21 is to provide sensor information (code information) such as correction information, the type of biosensor, etc. In the case where the code electrode 21 is to provide the correction information (i.e., in the case where the sensor information is the correction information assigned to each code), the measuring device recognizes the code of the corresponding biosensor from the code electrode 21 during measurement of the biosensor, corrects the measured value obtained from the working electrode by applying a predetermined correction value for each code, and then displays a final result value to the user. As such, in order that the code pattern portion 21a of the code electrode 21 may provide the correction information of the corresponding biosensor to the measuring device, it is necessary to pattern the code electrode 21 for each code during manufacturing of the biosensor such that a predetermined area of the code electrode 21 (in the reagent reaction layer where the reaction current flows) be in contact with the reagent reaction layer 14 in the code pattern portion 21a.

Figure 7:
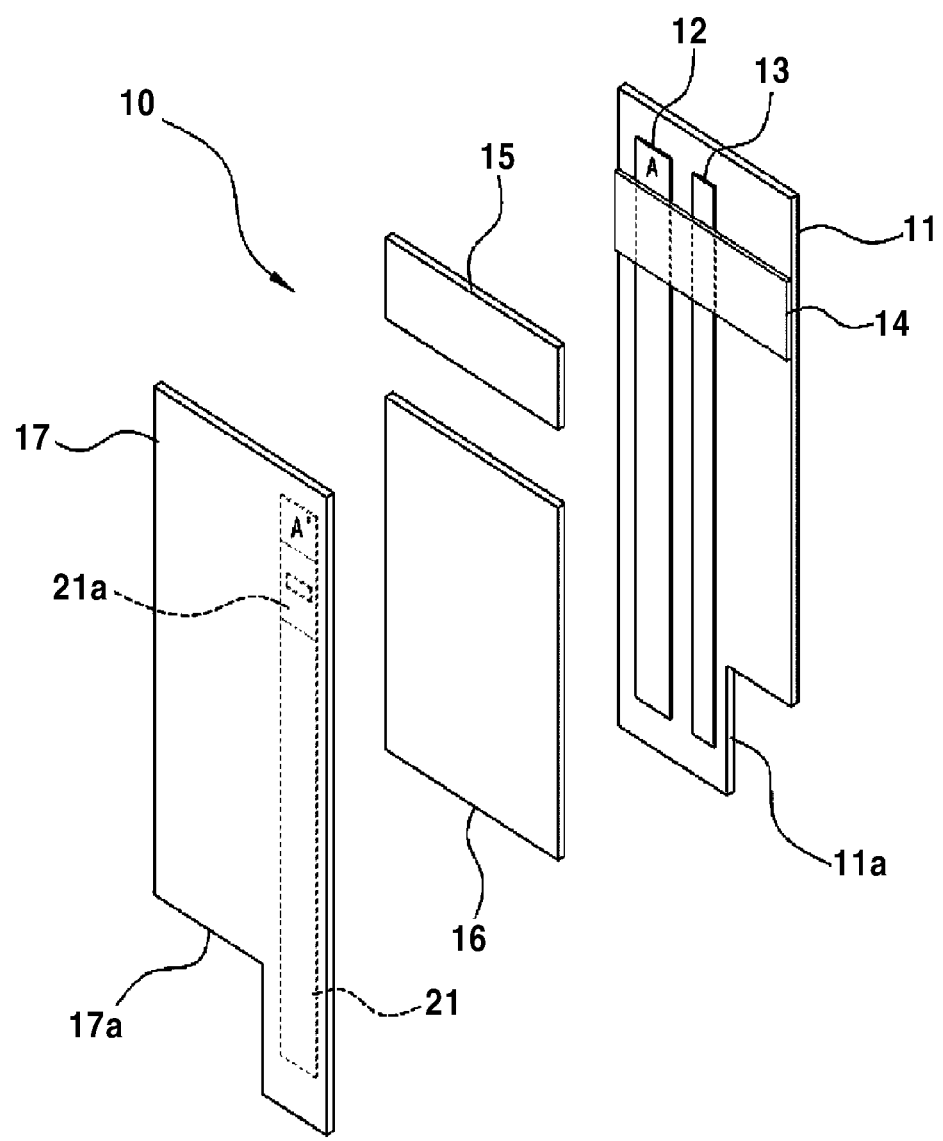
FIG. 7 is an exploded perspective view of a biosensor in accordance with another preferred embodiment of the present invention.

FIG. 7 is an exploded perspective view of a biosensor in accordance with another preferred embodiment of the present invention. Although the embodiment of FIGS. 3 to 6 forms the code electrode 21 on the lower insulating substrate 11, a code electrode 21 of the embodiment of FIG. 7 which is in contact with the reagent reaction layer 14 is formed on an upper insulating substrate 17.

That is, the code electrode 21 is formed on a lower surface (i.e., inner surface) of the upper insulating substrate 17 in the longitudinal direction, and a pattern is formed on the code electrode 21 using a laser beam. Then, the upper insulating substrate 17 on which the code electrode 21 is formed is assembled on a lower insulating substrate 11 with spacers 15 and 16 interposed therebetween.

In this case, only the working electrode 12 and the reference electrode 13 are formed on the lower insulating substrate 11, and the reagent reaction layer 14 is fixed on the working electrode 12 and the reference electrode 13 to intersect the electrodes. On the contrary, the code electrode 21 is formed on the upper insulating substrate 17 assembled with the lower insulating substrate 11 to be in contact with the reagent reaction layer 14, and a region of the code electrode 21 which is in contact with the reagent reaction layer 14 is patterned by a laser beam to form a code pattern portion 21a. After patterning, when the lower insulating substrate 11 is assembled with the upper insulating substrate 17 such that the code pattern portion 21a of the code electrode 21 is brought into contact with the reagent reaction layer 14, the biosensor 10 having the code electrode 21 is completed.

In the embodiment of FIG. 7, there is a difference that the code electrode 21 is assembled with the reagent reaction layer 14 of the lower insulating substrate 11 after it is formed on the upper insulating substrate 17. Moreover, connection terminals of the upper and lower insulating substrates 17 and 11 facing the respective electrodes 12, 13, and 21 are appropriately cut such that the respective electrodes 12, 13, and 21 are exposed through the connection terminals and connected to socket terminals of the measuring device. The respective electrodes 12, 13, and 21 of the biosensor are exposed through the cut portions 11a and 17a. Except for the above structure, the shapes of the electrodes and the code recognition method are substantially the same as those of the embodiment of FIGS. 3 to 6.

In the embodiment of FIG. 7, the pattern of the code electrode 21 may be formed by a laser ablation process. That is, after forming the code electrode 21 on the lower surface of the upper insulating substrate 17, the lower surface of the upper insulating substrate 17 may be ablated to a depth of the code electrode 21 using a laser beam such that only a specific region of the code electrode 21 may be removed from the upper insulating substrate 17. Alternatively, a specific region of the code electrode 21 and the upper insulating substrate 17 may be all removed by punching the upper surface of the upper insulating substrate 17 (the surface opposite to the surface where the code electrode 21 is formed, i.e., the outer surface, or the rear surface of the upper insulating substrate 17) using a laser beam (the substrate and the electrode are punched using a laser beam in the region where the electrode is to be removed).

When the code electrode 21 is formed on the upper insulating substrate 17 in the above manner, it is possible to prevent the reagent reaction layer 14 (fixed on the lower insulating substrate) from being damaged by high temperature during laser processing, and it is thus possible to ensure the stability of the reagent reaction layer and the electrode.

Figure 8:
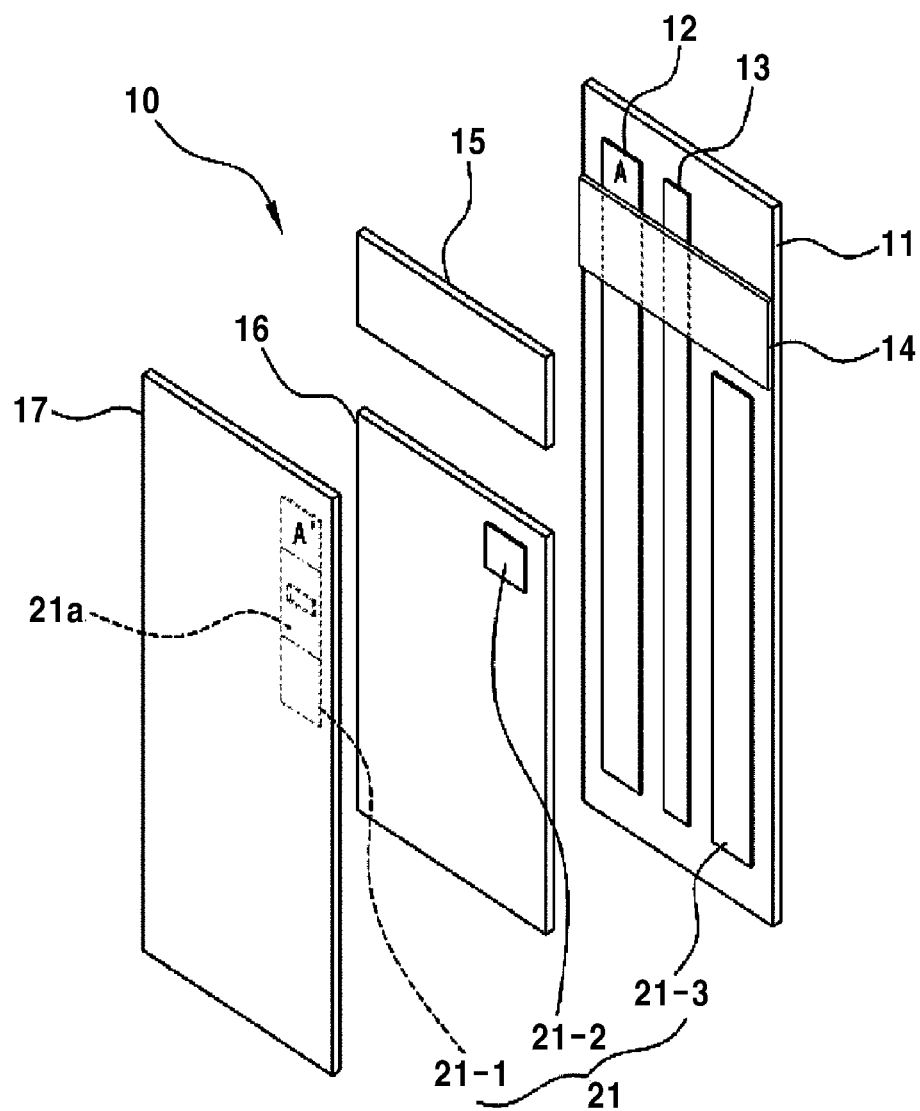
FIG. 8 is an exploded perspective view of a biosensor in accordance with still another preferred embodiment of the present invention.

FIG. 8 is an exploded perspective view of a biosensor for preventing damage of a reagent reaction layer in accordance with still another preferred embodiment of the present invention.

As shown in FIG. 8, a working electrode 12 and a reference electrode 13 are formed on a lower insulating substrate 11, and a reagent reaction layer 14 is fixed (along a sample path) on the working electrode 12 and the reference electrode 13 to intersect the electrodes.

In this case, a code electrode 21 includes a first code electrode portion 21-1 formed on a lower surface (i.e., inner surface) of an upper insulating substrate 17 to be in contact with the reagent reaction layer 14, an intermediate conductive portion 21-2 fixed on a spacer 16 to be connected to one end of the first code electrode portion 21-1, and a second code electrode portion 21-3 formed on an upper surface (i.e., inner surface) of the lower insulating substrate 11, in which one end thereof is connected to the intermediate conductive portion 21-2 of the spacer 16 and the other end thereof is exposed at a connection terminal of the biosensor and connected to the socket terminal of the measuring device in the same manner as the working electrode 12 and the reference electrode 13.

Here, the first code electrode portion 21-1 is formed in the longitudinal direction to pass through the reagent reaction layer 14 fixed on the lower insulating substrate 11 and has a code pattern portion 21a for providing sensor information. That is, a part of the first code electrode portion 21-1 in a predetermined area for each code is removed to form the code pattern portion 21a so as to provide the sensor information. In this embodiment, the pattern of the code electrode 21 may be formed using a laser beam in the same manner as the previous embodiments.

The second code electrode portion 21-3 is formed on the lower insulating substrate 11 in the longitudinal direction and has a structure in which the other end is exposed after the upper insulating substrate 17 is assembled with the lower insulating substrate 11. The exposed portion is to be connected to the socket terminal of the measuring device.

The intermediate conductive portion 21-2 is formed on the spacer 16 to electrically connect the first code electrode portion 21-1 of the upper insulating substrate 17 and the second code electrode portion 21-3 of the lower insulating substrate 11 (both sides of the intermediate conductive portion are connected to the first and second code electrode portions). The first and second code electrode portions 21-1 and 21-3 form the single code electrode 21 by the intermediate conductive portion 21-2.

In the code electrode 21 that is formed by the first code electrode portion 21-1, the second code electrode portion 21-3, and the intermediate conductive portion 21-2, its role and function, the configuration of the code pattern portion 21a, and the code recognition method are substantially the same as those of the previous embodiments. And, there is no difference from the code electrode described in the previous embodiments except that the first code electrode portion 21-1 of the upper insulating substrate 17 and the second code electrode portion 21-3 of the lower insulating substrate 11 are separately formed and then electrically connected to each other by the intermediate conductive portion 21-2 of the spacer 16 to form the single code electrode 21. Moreover, the process of patterning a specific region of the first code electrode portion 21-1 formed on the upper insulating substrate 17, which is in contact with the reagent reaction layer 14, using a laser beam, that is, the process of forming the code pattern portion 21a is substantially the same as the embodiment of FIG. 7 (the pattern is formed on the lower surface of the upper insulating substrate using a laser beam, or the upper surface of the upper insulating substrate is punched using a laser beam).

As such, in the embodiment of FIG. 8, a part of the code electrode (i.e., the first code electrode portion) which is in contact with the reagent reaction layer 14 is formed on the upper insulating substrate 17 so as to prevent the reagent reaction layer 14 from being damaged, and another part of the code electrode (i.e., the second code electrode portion) that is connected to the socket terminal of the measuring device is formed on the lower insulating substrate 11 such that the code electrode 21 is connected to the measuring device on the lower insulating substrate 11 in the same manner as the working electrode 12 and the reference electrode 13.

In the embodiment of FIG. 8, since the working electrode 12, the reference electrode 13, and the code electrode 21 are all connected to the socket terminals of the measuring device on the lower insulating substrate 11, it is possible to eliminate the process of cutting a specific region of the lower insulating substrate 11 and the upper insulating substrate 17 to expose the respective electrodes and connect the electrodes to the measuring device like the embodiment of FIG. 7. Instead, the length of the upper insulating substrate 17 may be reduced such that the electrodes of the lower insulating substrate 11 can be exposed and connected to the measuring device.

Figure 9:
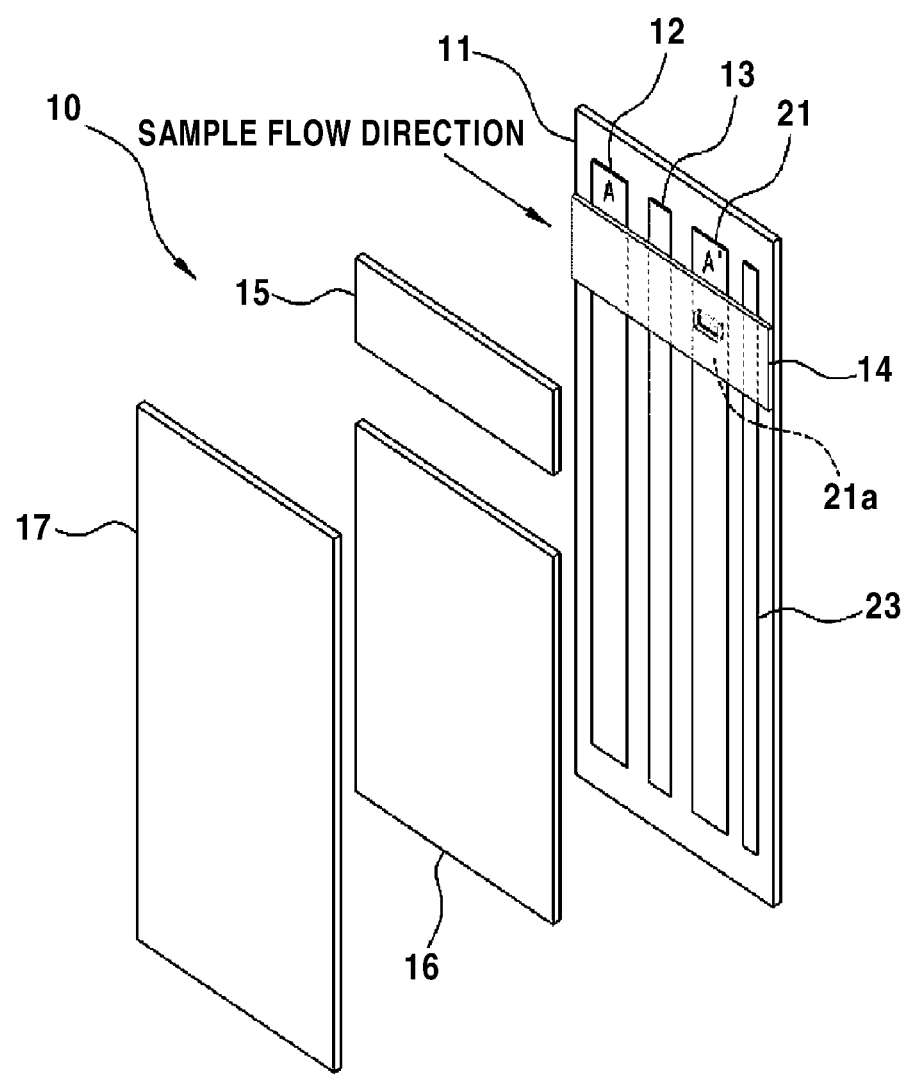
FIGS. 9 and 10 are exploded perspective views of a biosensor in accordance with yet another preferred embodiment of the present invention.
Figure 10:
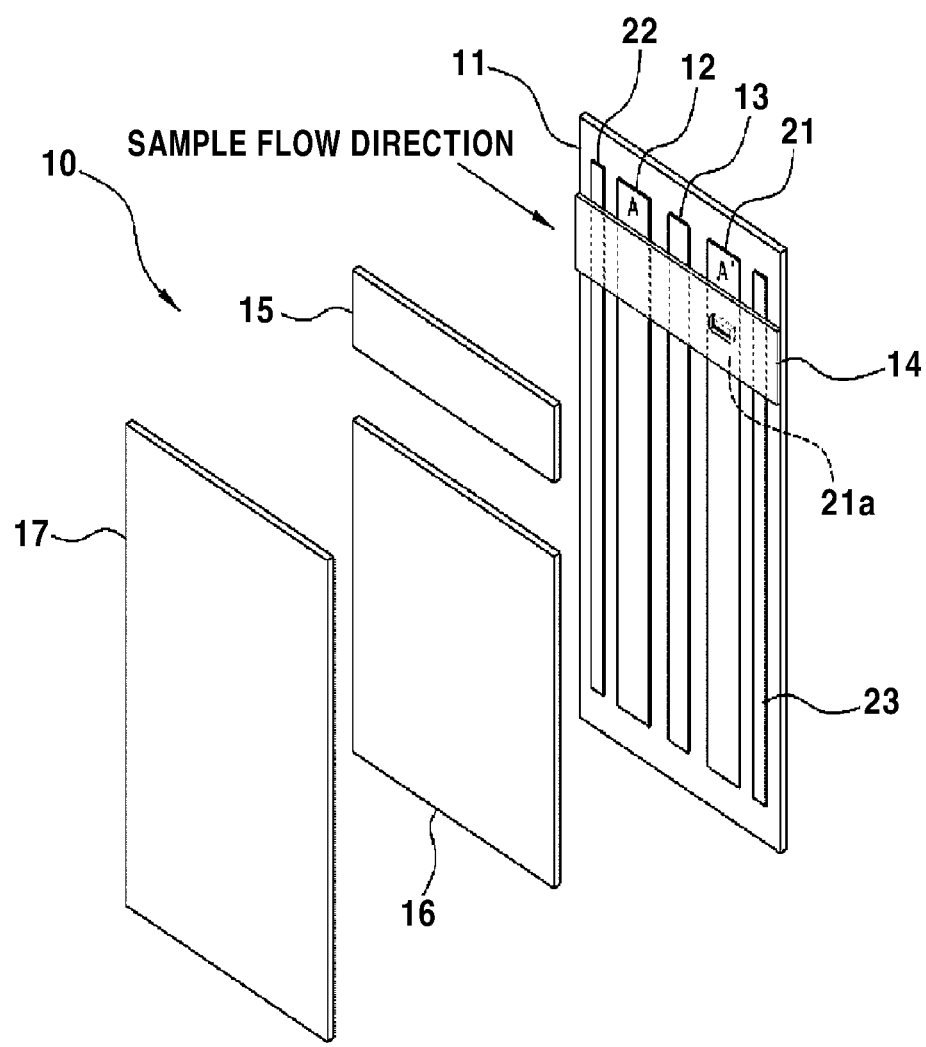

FIGS. 9 and 10 are exploded perspective views of a biosensor including a code electrode 21 and an electrode 23 for detecting a sample (hereinafter referred to as a sensing electrode) in accordance with yet another preferred embodiment of the present invention.

In the embodiment of FIG. 9, a working electrode 12, a reference electrode 13, a code electrode 21, and a sensing electrode 23 are formed in parallel with each other on an upper surface of a lower insulating substrate 11. The respective electrodes are formed in the longitudinal direction of the biosensor 10, and a reagent reaction layer 14 is fixed on the electrodes to intersect the electrodes.

Referring to FIG. 9, the working electrode 12 as a first electrode, the reference electrode 13 as a second electrode, the code electrode 21 as a third electrode, and the sensing electrode 23 as a fourth electrode are arranged from upstream to downstream with respect to the flow direction of the sample.

Here, since the code electrode 21 is substantially the same as that of the previous embodiments, a further description thereof will be omitted.

In the biosensor 10 of this embodiment, when a sample has been injected through a sample inlet port, the sample flows along the sample path to sequentially pass through the working electrode 12, the reference electrode 13, and the code electrode 21 and then reaches the sensing electrode 23. Especially, at a time point at which the sample reaches the sensing electrode 23, an electrical signal is output from the sensing electrode 23.

In this embodiment, the sensing electrode is provided such that the measuring device can determine that a sufficient amount of sample has been filled in the sample path. Thus, is possible to prevent an error from occurring when a sufficient amount of sample does not pass through the code electrode 21, that is, to prevent the measuring device from recognizing another code from the code electrode 21 when the sample is not sufficiently filled in the sample path.

In the event that the sample flowing along the sample path is not sufficient and thus does not completely pass through the code electrode 21, the measuring device may recognize another code. Accordingly, the sensing electrode 23 which is in contact with the reagent reaction layer 14 is provided at the downstream side with respect to the flow direction of the sample so as to solve this problem.

As a result, when a sufficient amount of sample passes through the code electrode 21 and thus reaches the sensing electrode 23, the measuring device receives an electrical signal output from the sensing electrode 23 and detects a sample filled state. Only when the sample filled state is detected, the measuring device can recognize the code of the corresponding biosensor based on the electrical signal output from the code electrode 21.

If the measuring device does not detect the sufficient amount of sample through the sensing electrode 23, an error message may be displayed to warn the user to inject a sufficient amount of sample and, at the same time, the code recognition process becomes ineffective.

In the embodiment of FIG. 10, two sensing electrodes 22 and 23 are provided to allow the measuring device to determine the time point at which the sample is injected and the time point at which the sample is completely filled. The first sensing electrode 22, the working electrode 12, the reference electrode 13, the code electrode 21, and the second sensing electrode 23 are formed in parallel with each other on the upper surface of the lower insulating substrate 11. The respective electrodes are formed in the longitudinal direction of the biosensor 10, and the reagent reaction layer 14 is fixed on the electrodes to intersect the electrodes.

Referring to FIG. 10, the first sensing electrode 22 as a first electrode, the working electrode 12 as a second electrode, the reference electrode 13 as a third electrode, the code electrode 21 as a fourth electrode, and the second sensing electrode 23 as a fifth electrode are arranged from upstream to downstream with respect to the flow direction of the sample.

In the biosensor 10 of this embodiment, when a sample has been injected through a sample inlet port, the sample flows along the sample path to sequentially pass through the first sensing electrode 22, the working electrode 12, the reference electrode 13, and the code electrode 21 and then reaches the second sensing electrode 23. Especially, at a time point at which the sample reaches the first and second sensing electrodes 22 and 23, electrical signals are output from the two sensing electrode 22 and 23.

In this embodiment, the first sensing electrode 22 is provided such that the measuring device can determine the time point at which the sample is initially injected through the sample inlet port, and the second sensing electrode 23 is provided such that the measuring device can determine that a sufficient amount of sample is filled in the sample path.

The second sensing electrode 23 prevents an error from occurring when a sufficient amount of sample does not pass through the code electrode 21, that is, to prevent the measuring device from recognizing another code from the code electrode 21 when the sample is not sufficiently filled in the sample path.

In the event that the sample flowing along the sample path is not sufficient and thus does not completely pass through the code electrode 21, the measuring device may recognize another code. Accordingly, the second sensing electrode 23 which is in contact with the reagent reaction layer 14 is provided at the downstream side with respect to the flow direction of the sample so as to solve this problem.

As a result, when a sufficient amount of sample passes through the code electrode 21 and thus reaches the second sensing electrode 23, the measuring device receives an electrical signal output from the second sensing electrode 23 and detects a sample filled state. Only when the sample filled state is detected, the measuring device can recognize the code of the corresponding biosensor based on the electrical signal output from the code electrode 21.

In this embodiment, when the measuring device determines the time point at which the sample is initially injected and the time point at which the sample is completely filled based on the signals output from the first sensing electrode 22 and the second sensing electrode 23, it is possible to measure the time between the two time points since the distance between the first and second sensing electrodes 22 and 23 is known, and thus it is possible to determine the characteristics of the sample, such as the flow characteristics of the sample and the flow rate.

Moreover, if the time until the sample is completely filled is accurately measured, the measured time can be used as a means for obtaining a correction coefficient used to correct the error in the measured value according to a difference in reactivity (the flow characteristics of the sample).

In more detail, since the flow rate of the sample may differ according to the flow characteristics of the sample, it is possible to estimate the properties of the sample from the difference in flow rate. Moreover, the flow characteristics of the sample may affect the measurement result and cause an error. Accordingly, if the difference in reactivity according to the properties of the sample is measured numerically by a test and stored in the measuring device, it is possible to correct the difference in reactivity by measuring the flow rate.

For example, in the case where blood is used as the sample, if the number of red blood cells is low, the solubility of the reagent (enzyme reaction layer) is increased to increase the reactivity, and thus the measured value is increased. On the contrary, if the number of red blood cells is high, the solubility is reduced to decrease the reactivity. Moreover, the number of red blood cells is in inverse proportion to the flow rate of blood, and thus if the measuring device calculates the number of red blood cells by measuring the flow rate of blood, it is possible to correct the difference in reactivity.

As such, in this embodiment, it is possible to accurate determines the time point at which the sample is injected and the time point at which the sample is completely filled, and thus it is possible to accurately correct the measurement result by obtaining the flow rate of the sample from the determined time points.

Figure 11:
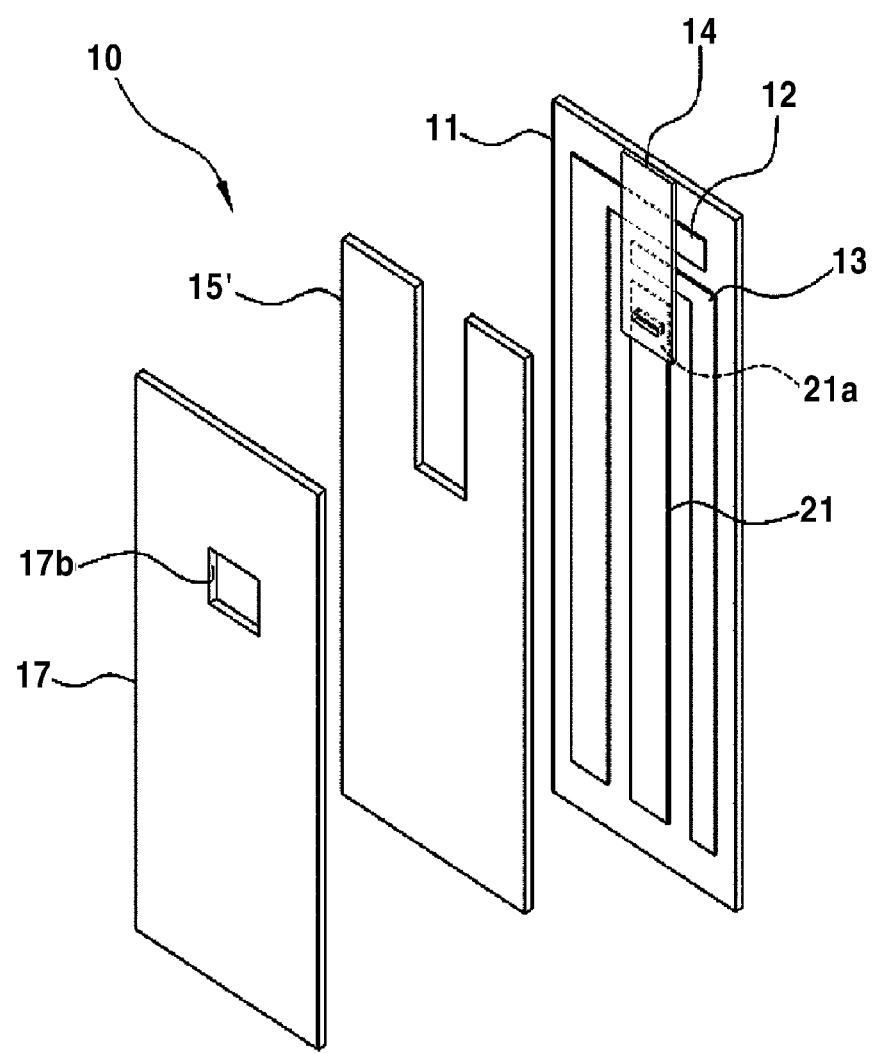
FIGS. 11 and 12 are exploded perspective views of a biosensor in accordance with still yet another preferred embodiment of the present invention.
Figure 12:
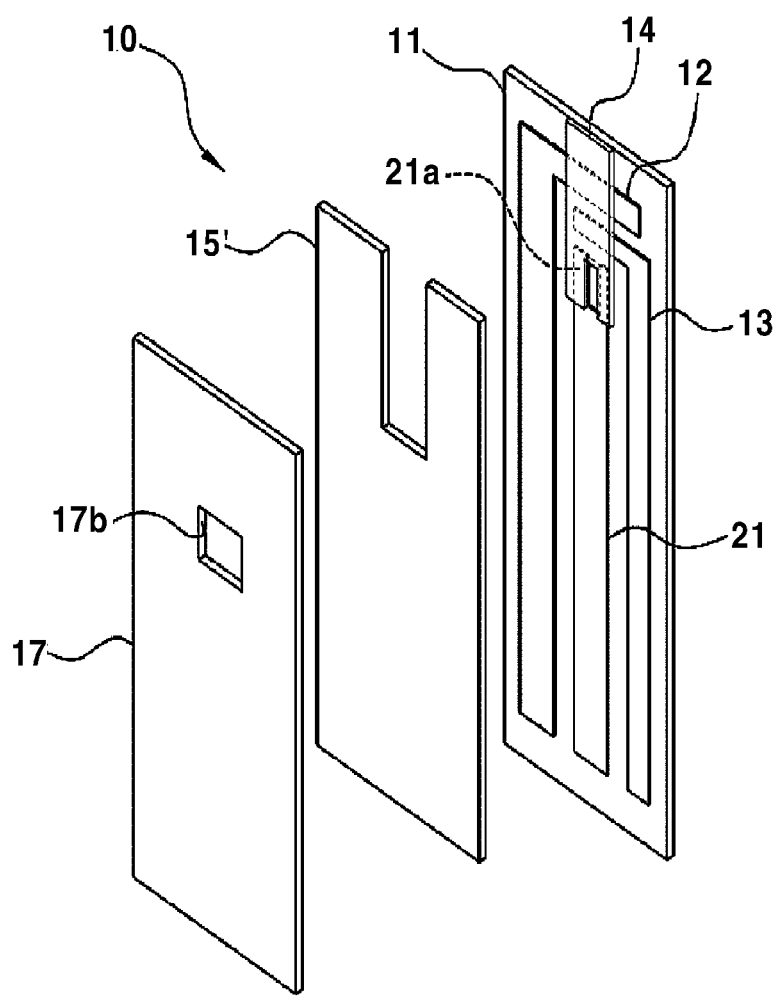
Figure 13:
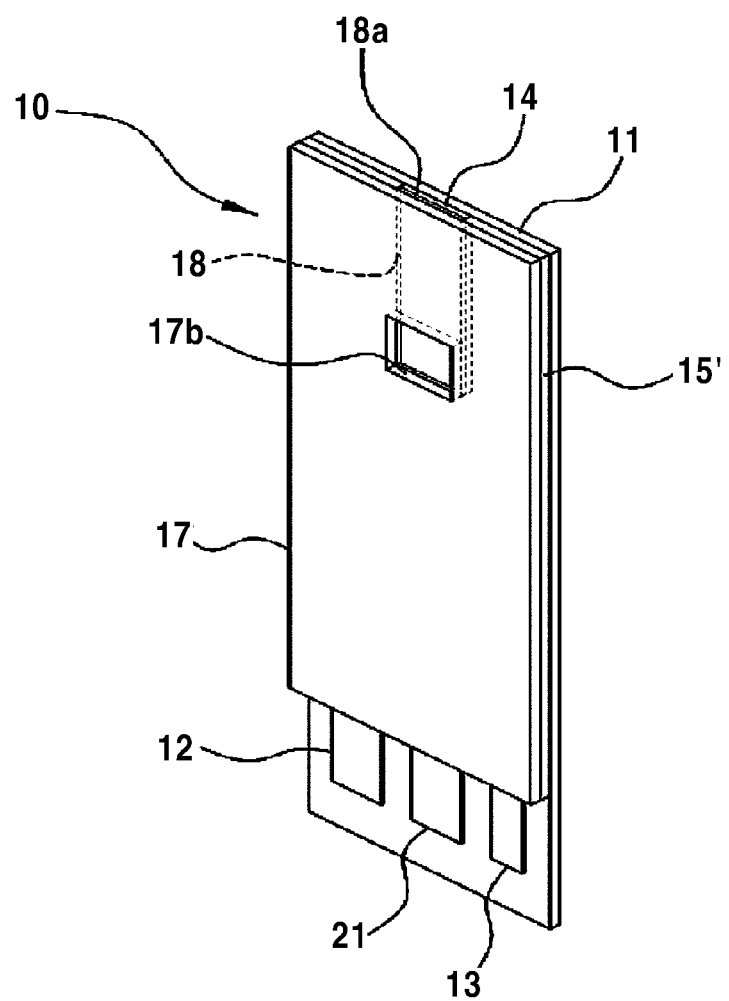
FIG. 13 is an assembled perspective view of the biosensor shown in FIGS. 11 and 12.

FIGS. 11 and 12 are exploded perspective views of a biosensor in accordance with still yet another preferred embodiment of the present invention, and FIG. 13 is an assembled perspective view of the biosensor shown in FIGS. 11 and 12.

In the previous embodiments, the sample inlet port is located at a side edge of the biosensor, and the reagent reaction layer is fixed on the electrodes in the width direction of the biosensor such that the sample path is formed in the width direction of the biosensor.

On the contrary, in the embodiment of FIGS. 11 to 13, a working electrode 12, a reference electrode 13, and a code electrode 21 having a code pattern portion 21a are formed on a lower insulating substrate 11. Especially, a sample inlet port 18a is located at an end of the biosensor and a reagent reaction layer 14 is fixed on the electrodes in the longitudinal direction of the biosensor 10 such that a sample path 18 is arranged in the longitudinal direction of the biosensor 10.

In order to form the reagent reaction layer 14 and the sample path 18 in the longitudinal direction of the biosensor 10, an end portion of each of the working electrode 12 and the reference electrode 13 extends in the width direction, and the reagent reaction layer 14 is fixed on the extended electrodes to intersect the extended electrodes.

Moreover, the code electrode 21 is formed between the working electrode 12 and the reference electrode 13 in the longitudinal direction of the biosensor 10, and the reagent reaction layer 14 is fixed on one end of the code electrode 21 such that the code electrode 21 is in contact with the reagent reaction layer 14.

A code pattern portion 21a patterned by removing a specific region of the code electrode 21 in a predetermined area for each code is formed on one end of the code electrode 21 which is in contact with the reagent reaction layer 14 such that the measuring device can recognize the code of the corresponding biosensor 10.

In this embodiment, since the code electrode 21 is substantially the same as that of the previous embodiments, a further description thereof will be omitted.

In the embodiment of FIGS. 11 to 13, a spacer 15' has a structure that allows the sample path 18 to be formed in the longitudinal direction of the biosensor 10. Thus, one end of the spacer 15' is cut in an area corresponding to the area of the reagent reaction layer 14 in the longitudinal direction of the biosensor 10. Reference numeral 17b denotes an air outlet port located at an end of the sample path 18 and formed on an upper insulating substrate 17.

Figure 14:
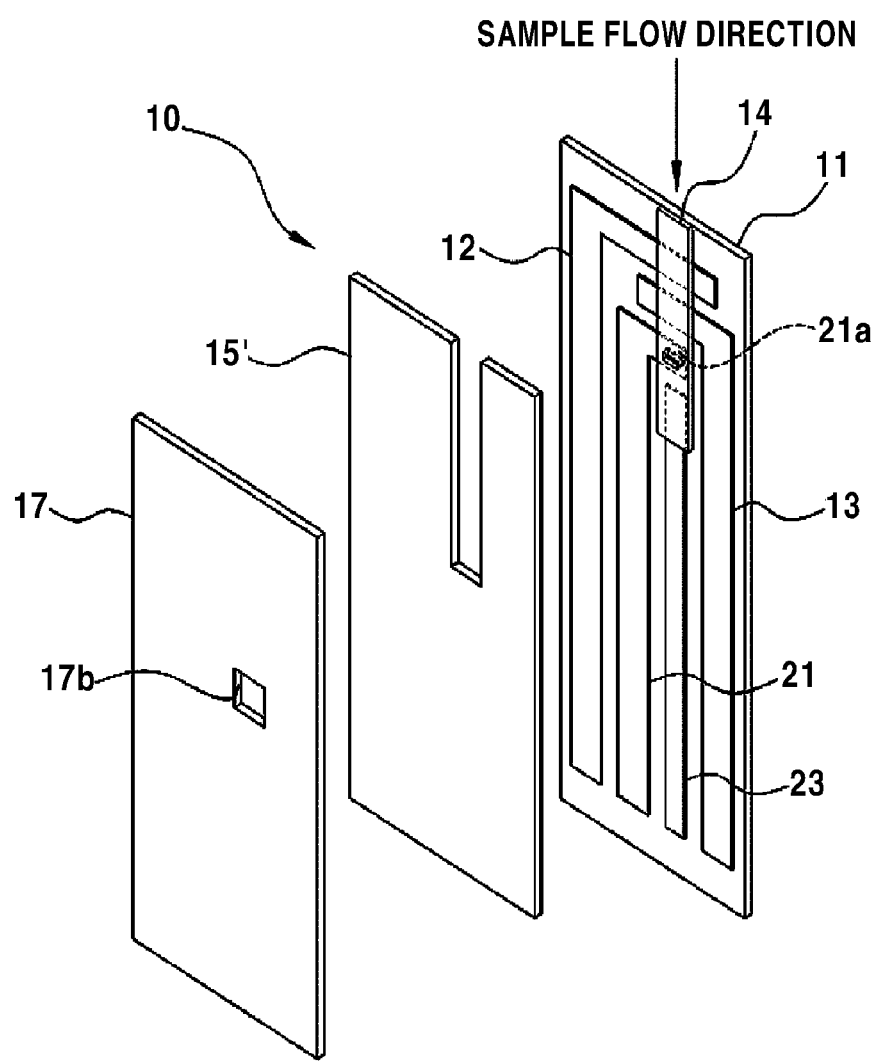
FIGS. 14 and 15 are exploded perspective views of a biosensor in accordance with a further preferred embodiment of the present invention.
Figure 15:
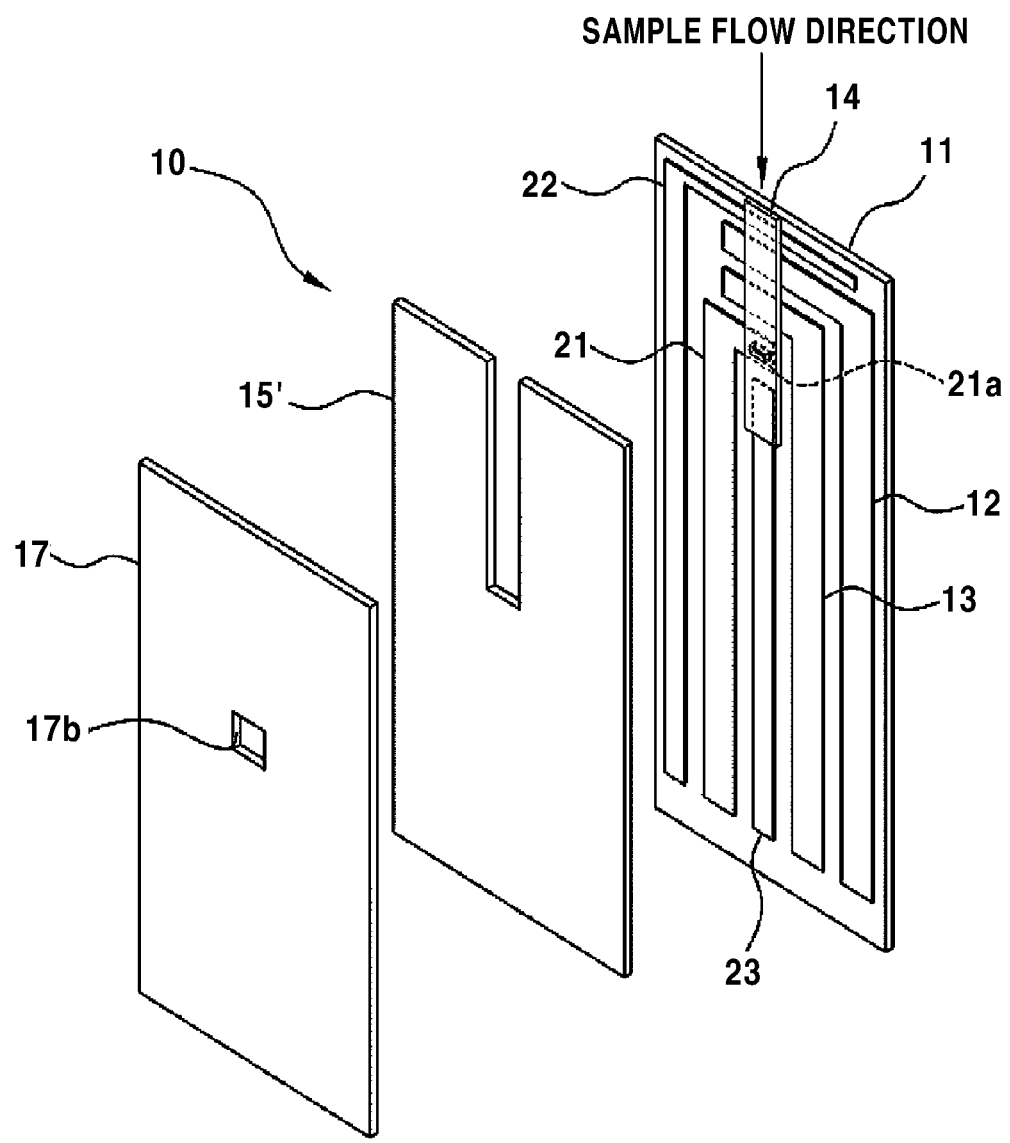

FIGS. 14 and 15 are exploded perspective views of a biosensor in accordance with a further preferred embodiment of the present invention.

In this embodiment of FIGS. 14 and 15, a sensing electrode is added to the embodiment of FIG. 11. Especially, in the embodiment of FIG. 14, the sensing electrode 23 for determining the sample filled state described in the embodiment of FIG. 9 is additionally provided, and in the embodiment of FIG. 15, the first sensing electrode 22 for determining the sample injection time point and the second sensing electrode 23 for determining the sample filled state described in the embodiment FIG. 10 are additionally provided.

First, in the embodiment of FIG. 14, a working electrode 12, a reference electrode 13, and a code electrode 21 are stacked on a lower insulating substrate 11 in the longitudinal direction of the biosensor 10, and an end portion of each of the electrodes 12, 13, and 21 extends in the width direction.

Moreover, the sensing electrode 23 for determining the sample filled state is arranged between the reference electrode 13 and the code electrode 21 on the lower insulating substrate 11 in the longitudinal direction of the biosensor 10, and a reagent reaction layer 14 is fixed on the extended electrodes 12, 13, and 21 to extend to an end portion of the sensing electrode 23 in the longitudinal direction of the biosensor 10.

As a result, when the lower insulating substrate 11 is assembled with an upper insulating substrate 17 with a spacer 15' interposed therebetween, a sample path 18 is formed in the width direction along the reagent reaction layer 14, and a sample inlet port 18a is located at an end of the biosensor 10.

The electrodes are arranged in an order of the working electrode 12, the reference electrode 13, the code electrode 21, and the sensing electrode 23 for determining the sample filled state from upstream to downstream with respect to the flow direction of the sample in the sample path 18 in the same manner as the embodiment of FIG. 9.

In the embodiment of FIG. 15, a first sensing electrode 22 (for determining a sample injection time point), a working electrode 12, a reference electrode 13, and a code electrode 21 are formed on a lower insulating substrate 11 in the longitudinal direction of the biosensor 10, and an end portion of each of the electrodes 22, 12, 13, and 21 extends in the width direction.

Moreover, a second sensing electrode 23 (for determining a sample filled state) is arranged between the reference electrode 13 and the code electrode 21 on the lower insulating substrate 11 in the longitudinal direction of the biosensor 10, and a reagent reaction layer 14 is fixed on the extended electrodes 22, 12, 13, and 21 to extend to an end portion of the second sensing electrode 23 in the longitudinal direction of the biosensor 10.

As a result, when the lower insulating substrate 11 is assembled with an upper insulating substrate 17 with a spacer 15' interposed therebetween, a sample path 18 is formed in the width direction along the reagent reaction layer 14, and a sample inlet port 18a is located at an end of the biosensor 10.

The electrodes are arranged in an order of the first sensing electrode 22, the working electrode 12, the reference electrode 13, the code electrode 21, and the second sensing electrode 23 from upstream to downstream with respect to the flow direction of the sample in the sample path 18 in the same manner as the embodiment of FIG. 10.

In the embodiment of FIGS. 14 and 15, the roles and functions of the code electrode and the sensing electrode (including the first and second sensing electrodes) are substantially the same as those of the previous embodiments.

Figure 16:
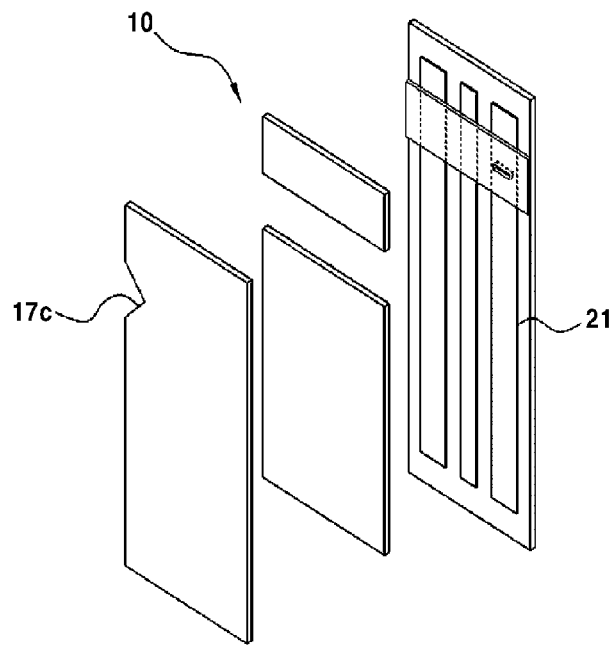
FIGS. 16 and 17 are exploded perspective views of a biosensor in accordance with another further preferred embodiment of the present invention.
Figure 17:
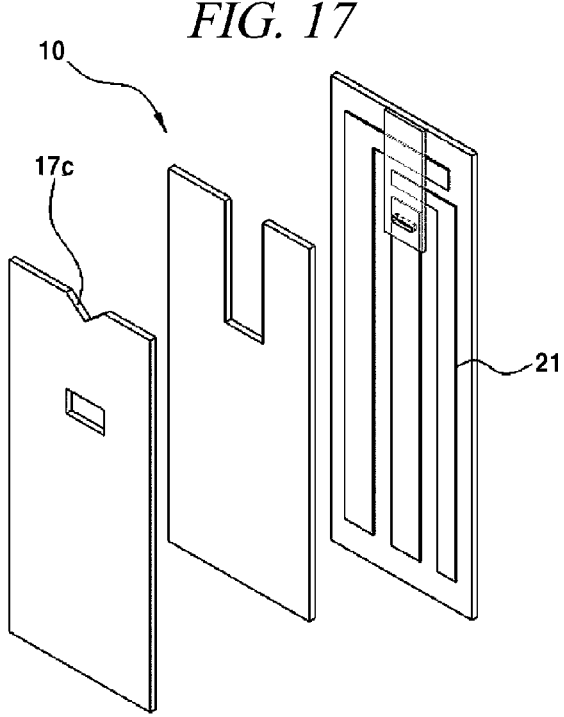

FIGS. 16 and 17 are exploded perspective views of a biosensor in accordance with another further preferred embodiment of the present invention.

The present embodiment provides a biosensor including a notch portion 17c formed around a sample inlet port so as to prevent the sample inlet port from being clogged by a user's body (e.g. the fingertip of user) being in contact with the sample inlet port when a blood sample is introduced through the sample inlet port.

The notch portion 17c may be formed around the sample inlet port on any one of an upper insulating substrate 17 and a lower insulating substrate 11.

Figure 18A:
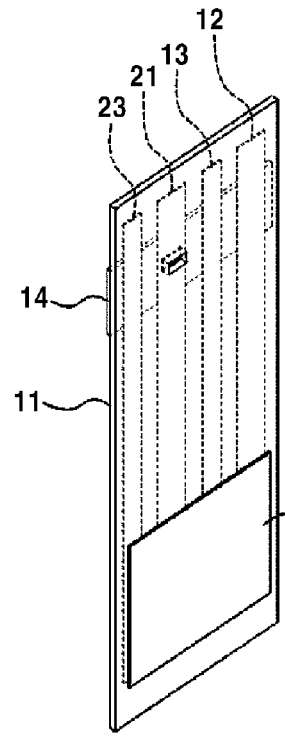
FIGS. 18 and 19 are exploded perspective views of a biosensor in accordance with still another further preferred embodiment of the present invention.
Figure 18B:
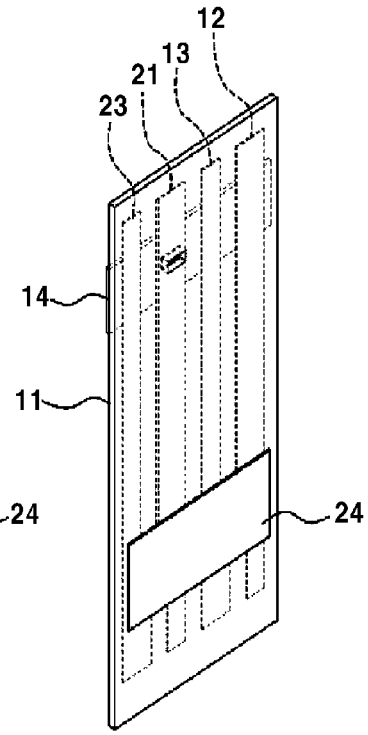
Figure 18C:
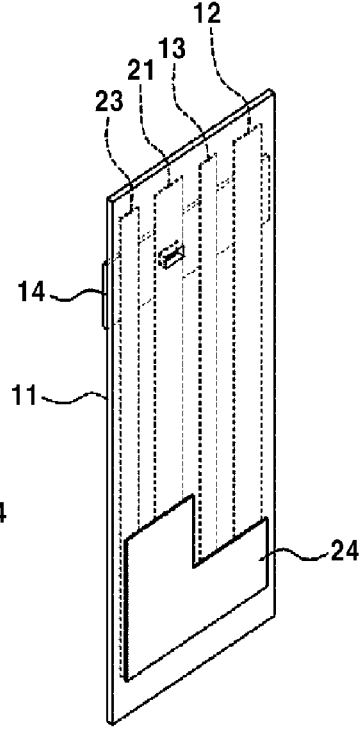
Figure 19:
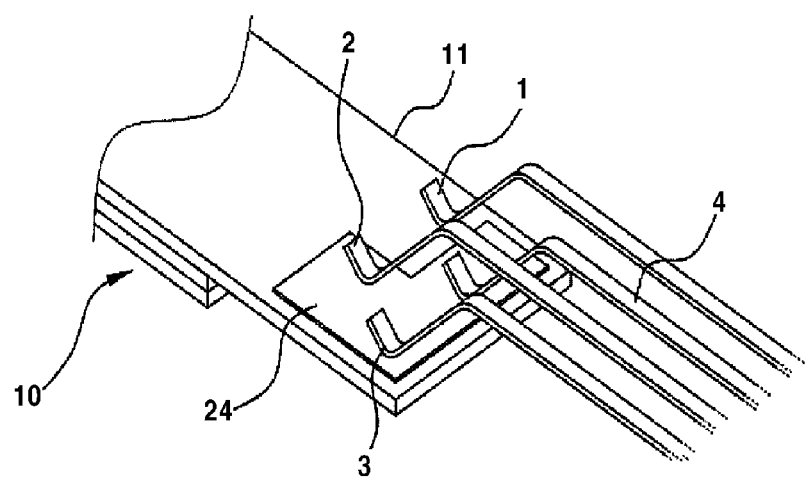

FIGS. 18 and 19 are exploded perspective views of a biosensor in accordance with still another further preferred embodiment of the present invention, in which a code recognition electrode 24 is provided in addition to the code electrode 21 (a spacer and an upper insulating substrate are not shown).

As shown in FIGS. 18 and 19, the additionally provided code recognition electrode 24 is formed on the rear surface (i.e., lower surface or outer surface) of a lower insulating substrate 11. Like the code electrode 21 provided in the biosensor 10, the code recognition electrode 24 also provides sensor information. For example, in the case where the code electrode 21 provides correction information of the corresponding biosensor, the code recognition electrode 24 additionally provided on the rear surface of the lower insulating substrate 11 may provide information on the type of biosensor such that measuring device can identify the type of biosensor. On the contrary, in the case where the code electrode 21 provides information on the type of biosensor such that measuring device can identify the type of biosensor, the code recognition electrode 24 of the lower insulating substrate 11 may provide correction information of the corresponding biosensor.

The code recognition electrode 24 should have a predetermined electrode pattern for each code such that the measuring device can identify the biosensor in the same manner as the code electrode 21. The shape of the code recognition electrode 24 may differ according to the code and the sensor information to be provided.

As a result, when the biosensor 10 including the code recognition electrode 24 having a different shape is inserted into the socket of the measuring device, terminals 1 to 4 installed inside the socket of the measuring device recognize the electrode having a different shape for each code such that the measuring device can identify the corresponding biosensor 10 classified according to the code and the sensor information.

In more detail, in the case where the shapes of the code recognition electrode 24 differ according to the code and the sensor information as shown in (a) to (c) of FIG. 18, the socket terminals are turned on and off according to the shape of the electrode.

For example, in the case where the biosensor 10 having the code recognition electrode 24 as shown in (c) of FIG. 18 is inserted into the socket of the measuring device, an OFF signal is transmitted to a first terminal 1 of the socket, and an ON signal is transmitted to second to fourth terminals 2 to 4.

On the contrary, in the case where the biosensor 10 having the code recognition electrode 24 as shown in (a) of FIG. 18 is inserted into the socket of the measuring device, an ON signal is transmitted to all terminals 1 to 4 of the socket, and in the case where the biosensor 10 having the code recognition electrode 24 as shown in (b) of FIG. 18 is inserted into the socket of the measuring device, an ON signal is transmitted to the first and second terminals 1 and 2 and an OFF signal is transmitted to the third and fourth terminals 3 and 4.

As such, when the biosensor 10 to which a different code is assigned is inserted into the socket of the measuring device, the measuring device recognizes the code of the biosensor 10 from the code recognition electrode 24, thereby obtaining the information on the corresponding biosensor 10.

For example, in the case where the code recognition electrode 24 provides correction information, the measuring device recognizes the code of the corresponding biosensor 10 based on the shape of the code recognition electrode 24 and corrects the measured value with a predetermined correction value for each code, thus displaying an accurate result value.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. A biosensor, in which a working electrode and a reference electrode are formed on an inner surface of a lower insulating substrate, a reagent reaction layer is fixed on the inner surface of the lower insulating substrate along a sample path to be in contact with the working electrode and the reference electrode, and an upper insulating substrate is assembled with the lower insulating substrate with a spacer interposed therebetween to form the sample path,
   wherein a code electrode outputs an electrical signal according to a reaction between a sample and the reaction reagent layer, and provides the electrical signal to a measuring device,
   wherein the code electrode comprises a code pattern portion, formed by patterning the code electrode at a position which is in contact with the reagent reaction layer, wherein an area of the code pattern portion is varied according to sensor information, wherein the code electrode is configured to output the electrical signal according to the sensor information, and
   wherein the code pattern portion is patterned by removing a predetermined area of the code electrode such that the contact area with the reagent reaction layer, in which reaction current flows, differs according to a code assigned to a corresponding biosensor based on the sensor information.

2. The biosensor of claim 1, wherein the code pattern portion is formed by removing a predetermined area of the code electrode in a longitudinal direction or a width direction of the code electrode.

3. The biosensor of claim 1, wherein the code electrode is formed on the inner surface of the lower insulating substrate.

4. The biosensor of claim 3, wherein, the code pattern portion is formed by ablating the predetermined area of the code electrode together with the reagent reaction layer with irradiating a laser beam onto the inner surface of the lower insulating substrate.

5. The biosensor of claim 3, wherein, the code pattern portion is formed by ablating the predetermined area of the code electrode together with the lower insulating substrate with irradiating a laser beam onto an outer surface of the lower insulating substrate.

6. The biosensor of claim 1, wherein the code electrode is formed on an inner surface of the upper insulating substrate.

7. The biosensor of claim 6, wherein, the code pattern portion is formed by ablating the predetermined area of the code electrode with irradiating a laser beam onto the inner surface of the upper insulating substrate.

8. The biosensor of claim 6, wherein, the code pattern portion is formed by ablating the predetermined area of the code electrode together with the upper insulating substrate with irradiating a laser beam onto an outer surface of the upper insulating substrate.

9. The biosensor of claim 1, wherein the code electrode comprises:
   a first code electrode portion formed on the inner surface of the upper insulating substrate to be in contact with the reagent reaction layer;
   an intermediate conductive portion fixed on the spacer to be connected to one end of the first code electrode portion; and
   a second code electrode portion formed on the inner surface of the lower insulating substrate such that one end thereof is connected to an intermediate conductive portion of the spacer and an other end thereof is connected to a socket terminal of the measuring device.

10. The biosensor of claim 1, wherein the sensor information is correction information of the corresponding biosensor or information on the type of the bio-sensor.

11. The biosensor of claim 1, wherein a notch portion formed by forming a notch on any one of the upper insulating substrate and the lower insulating substrate is provided around a sample inlet port of the sample path so as to prevent the sample inlet port from being clogged by a user's body being in contact with the sample inlet port.

12. The biosensor of claim 1, wherein a sample inlet port of the sample path is located at an end of the biosensor, and the sample path and the reagent reaction layer are arranged in a longitudinal direction of the biosensor.

13. The biosensor of claim 1, wherein a code recognition electrode for providing sensor information is additionally formed on an outer surface of the lower insulating substrate, the code recognition electrode having a different shape according to a code assigned to the corresponding biosensor based on the sensor information such that socket terminals of the measuring device can be distinguished according to the assigned code.

14. The biosensor of claim 1, wherein a sensing electrode for determining a sample filled state in the sample path is additionally formed to be in contact with the reagent reaction layer such that the electrodes are arranged in an order of the working electrode, the reference electrode, the code electrode, and the sensing electrode for determining the sample filled state with respect to a flow direction of the sample in the sample path.

15. The biosensor of claim 1, wherein a sensing electrode for determining a sample injection time point and a sensing electrode for determining a sample filled state in the sample path are additionally formed to be in contact with the reagent reaction layer such that the electrodes are arranged in an order of the sensing electrode for determining the sample injection time point, the working electrode, the reference electrode, the code electrode, and the sensing electrode for determining the sample filled state with respect to a flow direction of the sample in the sample path.

16. A method for manufacturing a biosensor having a code electrode, the method comprising:
    forming a working electrode and a reference electrode on an inner surface of a lower insulating substrate;
    forming a second code electrode portion on the inner surface of the lower insulating substrate such that one end thereof is connected to an intermediate conductive portion of a spacer and an other end thereof is connected to a socket terminal of a measuring device;
    fixing a reagent reaction layer on the inner surface of the lower insulating substrate along a sample path to be in contact with the working electrode and the reference electrode;
    forming a first code electrode portion, which is in contact with the reagent reaction layer, on an inner surface of an upper insulating substrate;
    forming a code pattern portion by patterning a specific region of the first code electrode portion, which is in contact with the reagent reaction layer, according to a code assigned to a corresponding biosensor based on sensor information; fixing the intermediate conductive portion on the spacer; and
    assembling the upper insulating substrate with the lower insulating substrate with the spacer interposed therebetween to form the sample path such that the intermediate conductive portion of the spacer connects the first code electrode portion and the second code electrode portion,
    wherein the code pattern portion is patterned by removing a predetermined area of the first code electrode portion such that the contact area with the reagent reaction layer, in which reaction current flows, differs according to the assigned code.

17. The method of claim 16, wherein, in forming the code pattern portion, the predetermined area of the first code electrode portion is ablated by irradiating a laser beam onto the inner surface of the upper insulating substrate.

18. The method of claim 16, wherein, in forming the code pattern portion, the predetermined area of the first code electrode portion is ablated together with the upper insulating substrate by irradiating a laser beam onto an outer surface of the upper insulating substrate.

19. A method for obtaining sensor information on a biosensor, the method comprising:
    providing the biosensor of;
    applying working voltage to the working electrode and injecting the sample into the sample path after the biosensor is inserted into the measuring device; and obtaining sensor information on the biosensor based on electrical signals output from the working electrode and the code electrode.

20. The method of claim 19, wherein the biosensor further comprises a sensing electrode for determining a sample filled state in the sample path, and the measuring device obtains the sensor information when the measuring device determines the sample filled state from an electrical signal output from the sensing electrode for determining the sample filled state.

* * * * *